US010363107B2

(12) United States Patent
Blumenkranz et al.

(10) Patent No.: US 10,363,107 B2
(45) Date of Patent: *Jul. 30, 2019

(54) WIRELESS FORCE SENSOR ON A DISTAL PORTION OF A SURGICAL INSTRUMENT AND METHOD

(71) Applicant: Intuitive Surgical Operations, Inc., Sunnyvale, CA (US)

(72) Inventors: Stephen J. Blumenkranz, Los Altos, CA (US); Brett J. Lockyer, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/938,440

(22) Filed: Mar. 28, 2018

(65) Prior Publication Data

US 2018/0214222 A1 Aug. 2, 2018

Related U.S. Application Data

(63) Continuation of application No. 14/107,692, filed on Dec. 16, 2013, now Pat. No. 9,943,375, which is a
(Continued)

(51) Int. Cl.
*A61B 17/00* (2006.01)
*A61B 34/30* (2016.01)
(Continued)

(52) U.S. Cl.
CPC ............. *A61B 34/30* (2016.02); *A61B 34/35* (2016.02); *A61B 34/37* (2016.02); *A61B 34/71* (2016.02);
(Continued)

(58) Field of Classification Search
CPC ......... A61B 34/30; A61B 34/35; A61B 34/37; A61B 34/71; A61B 34/76; A61B 90/10;
(Continued)

(56) References Cited

U.S. PATENT DOCUMENTS 3,515,137 A 6/1970 Santomieri
4,838,280 A 6/1989 Haaga
(Continued)

FOREIGN PATENT DOCUMENTS

EP 1650615 A1 4/2006
FR 2693397 A1 1/1994
(Continued)

OTHER PUBLICATIONS

Anagnostou, D., et al., "Improved Multiband Performance with Self-Similar Fractal Antennas", IEEE Topical Conference on Wireless Communication Technology, Oct. 15-17, 2003, pp. 271-272, IEEE.
(Continued)

*Primary Examiner* — Aaron F Roane
(74) *Attorney, Agent, or Firm* — Schwegman Lundbrg & Woessner, P.A.

(57) ABSTRACT

A surgical instrument includes a distal portion. A force sensor is operatively mounted on the distal portion. The force sensor includes a wireless package, which wirelessly provides (1) identification information of the surgical instrument and (2) strain data related to the distal portion. A surgical end effector includes a jaw and the distal portion is on a non-contact portion of the jaw. The wireless package includes a surface acoustic wave strain sensor with identification information. The wireless package also includes a small folded antenna electrically coupled to the surface acoustic wave strain sensor with identification information. The identification information includes an identification of a
(Continued)

type of surgical instrument and unique identification of the specific surgical instrument in the type of surgical instrument.

14 Claims, 19 Drawing Sheets

Related U.S. Application Data continuation of application No. 12/634,489, filed on Dec. 9, 2009, now Pat. No. 8,628,518, which is a continuation-in-part of application No. 11/864,974, filed on Sep. 29, 2007, now Pat. No. 8,375,808, which is a continuation-in-part of application No. 11/537,241, filed on Sep. 29, 2006, now Pat. No. 8,945,095.

(60) Provisional application No. 60/755,108, filed on Dec. 30, 2005.

(51) Int. Cl.
*A61B 90/10* (2016.01)
*A61B 34/00* (2016.01)
*A61B 34/37* (2016.01)
*A61B 34/35* (2016.01)
*A61B 90/98* (2016.01)
*A61B 17/29* (2006.01)
*A61B 90/00* (2016.01)

(52) U.S. Cl.
CPC .............. *A61B 34/76* (2016.02); *A61B 90/10* (2016.02); *A61B 90/98* (2016.02); *A61B 2017/00477* (2013.01); *A61B 2017/2929* (2013.01); *A61B 2034/305* (2016.02); *A61B 2090/064* (2016.02); *A61B 2562/08* (2013.01)

(58) Field of Classification Search
CPC .............. A61B 90/98; A61B 2034/305; A61B 2090/064; A61B 2017/00477; A61B 2017/2929; A61B 2562/08
USPC .......................................................... 606/1
See application file for complete search history.

(56) References Cited

U.S. PATENT DOCUMENTS

| | | | |
|---|---|---|---|
| 4,906,907 A | 3/1990 | Tsuchihashi et al. |
| 5,631,973 A | 5/1997 | Green |
| 5,779,697 A | 7/1998 | Glowa et al. |
| 5,784,542 A | 7/1998 | Ohm et al. |
| 5,807,326 A | 9/1998 | Oneill et al. |
| 5,807,377 A | 9/1998 | Madhani et al. |
| 5,864,092 A | 1/1999 | Gore et al. |
| 6,068,627 A | 5/2000 | Orszulak et al. |
| 6,120,433 A | 9/2000 | Mizuno et al. |
| 6,206,835 B1 | 3/2001 | Spillman, Jr. et al. |
| 6,231,565 B1 | 5/2001 | Tovey et al. |
| 6,259,991 B1 | 7/2001 | Nysen |
| 6,331,181 B1 | 12/2001 | Tierney et al. |
| 6,344,038 B1 | 2/2002 | Weber |
| 6,371,952 B1 | 4/2002 | Madhani et al. |
| 6,470,205 B2 | 10/2002 | Bosselmann et al. |
| 6,491,701 B2 | 12/2002 | Tierney et al. |
| 6,494,882 B1 | 12/2002 | Lebouitz et al. |
| 6,574,355 B2 | 6/2003 | Green |
| 6,587,750 B2 | 7/2003 | Gerbi et al. |
| 6,594,552 B1 | 7/2003 | Nowlin et al. |
| 6,676,684 B1 | 1/2004 | Morley et al. |
| 6,770,081 B2 | 8/2004 | Cooper et al. |
| 6,783,524 B2 | 8/2004 | Anderson et al. |
| 6,810,750 B1 | 11/2004 | Kiefer et al. |
| 6,817,974 B2 | 11/2004 | Cooper et al. |
| 6,835,173 B2 | 12/2004 | Couvillon, Jr. |
| 6,866,671 B2 | 3/2005 | Tierney et al. |
| 6,879,880 B2 | 4/2005 | Nowlin et al. |
| 6,902,560 B1 | 6/2005 | Morley et al. |
| 6,936,042 B2 | 8/2005 | Wallace et al. |
| 6,969,385 B2 | 11/2005 | Moreyra |
| 7,250,028 B2 | 7/2007 | Julian et al. |
| 7,357,774 B2 | 4/2008 | Cooper |
| 7,453,227 B2 | 11/2008 | Prisco et al. |
| 7,606,615 B2 | 10/2009 | Makower et al. |
| 7,648,513 B2 | 1/2010 | Green et al. |
| 7,678,075 B2 | 3/2010 | Wantink et al. |
| 7,824,401 B2 | 11/2010 | Manzo et al. |
| 7,842,028 B2 | 11/2010 | Lee |
| 8,004,229 B2 | 8/2011 | Nowlin et al. |
| 8,375,808 B2 | 2/2013 | Blumenkranz et al. |
| 8,613,230 B2 | 12/2013 | Blumenkranz et al. |
| 8,628,518 B2 * | 1/2014 | Blumenkranz ........ A61B 90/10 606/1 |
| 8,945,095 B2 | 2/2015 | Blumenkranz et al. |
| 9,943,375 B2 * | 4/2018 | Blumenkranz ........ A61B 90/10 |
| 2002/0111635 A1 | 8/2002 | Jensen et al. |
| 2002/0133174 A1 | 9/2002 | Charles et al. |
| 2002/0188294 A1 | 12/2002 | Couture et al. |
| 2003/0229286 A1 | 12/2003 | Lenker |
| 2004/0167515 A1 | 8/2004 | Petersen et al. |
| 2004/0215382 A1 | 10/2004 | Breed et al. |
| 2005/0200324 A1 | 9/2005 | Guthart et al. |
| 2006/0161136 A1 | 7/2006 | Anderson et al. |
| 2006/0161137 A1 | 7/2006 | Orban, III |
| 2006/0161138 A1 | 7/2006 | Orban, III |
| 2006/0235436 A1 | 10/2006 | Anderson et al. |
| 2007/0018958 A1 | 1/2007 | Tavakoli et al. |
| 2007/0078484 A1 | 4/2007 | Talarico et al. |
| 2007/0119274 A1 | 5/2007 | Devengenzo et al. |
| 2007/0137371 A1 | 6/2007 | Devengenzo et al. |
| 2007/0151391 A1 | 7/2007 | Larkin et al. |
| 2007/0156019 A1 | 7/2007 | Larkin et al. |
| 2007/0173873 A1 | 7/2007 | Ranucci et al. |
| 2008/0046122 A1 | 2/2008 | Manzo et al. |
| 2008/0147090 A1 | 6/2008 | Seibold et al. |
| 2009/0088775 A1 | 4/2009 | Swarup et al. |
| 2014/0100588 A1 | 4/2014 | Blumenkranz et al. |
| 2014/0107627 A1 | 4/2014 | Blumenkranz et al. |
| 2015/0164598 A1 | 6/2015 | Blumenkranz et al. |

FOREIGN PATENT DOCUMENTS

| | | | |
|---|---|---|---|
| JP | H06142114 A | 5/1994 |
| JP | H08224246 A | 9/1996 |
| JP | 9318469 A | 12/1997 |
| JP | 2002159509 A | 6/2002 |
| WO | WO-9825666 A1 | 6/1998 |
| WO | WO-2005039835 A1 | 5/2005 |
| WO | WO-2007111737 A2 | 10/2007 |
| WO | WO-2007120329 A2 | 10/2007 |
| WO | WO-2007126443 A2 | 11/2007 |

OTHER PUBLICATIONS

Brocato, Robert W., "Passive Wireless Sensor Tags" Sandia Report, Mar. 2006, pp. 1-20, Sandia National Laboratories, Albuquerque, NM, USA.
Cepolina F. et al., "Review of robotic fixtures for minimaliy invasive surgery," International Journal of Medical Robotics and Computer Assisted Surgery, 2004, pp. 43-63, vol. 1, Issue-1.
Co-pending U.S. Appl. No. 60/752,755, filed Dec. 20, 2005.
Fractus' Micro Reach XtendT 2.4GHz Antenna Sets New Standard for Antenna Miniaturisation, Fractus News, Mar. 6, 2007, pp. 1-2 [online], Fractus S.A., Retrieved on Jul. 9, 2010 from the Internet:< URL:http://www.fractus.com/main/fractus/news_english/fractus_ micro_ reach_xtend_24ghz_ antenna_ sets_new_standard_for_ antenna_minia/>. No author provided.
Fractus® Reach XtendT Chip Antenna, Data Sheet—Products & Services, 2007, 2 pages, Fractus S.A. No author provided.

(56) References Cited

OTHER PUBLICATIONS

Jones, Inke, et al, "Wireless RF Communication in Biomedical Applications", Smart Materials and Structures, 2008, 17 (1), IOP Publishing Ltd., UK, pp. 1-10.

Lonsdale A., "Dynamic Rotary Torque Measurement Using Surface Acoustic Waves", Sensors, Oct. 2001, 18 (10), Sensor Technology Ltd., UK, 51-56.

McDonald et al., "Small Fractal Antennas Princeton University, Princeton, NJ, USA. Retrieved from the Internet:< URL:http://www.hep.princeton.edu/~mcdonald/examples/fractal_antenna.pdf>.", Dec. 22, 2003, Princeton University, Princeton, NJ, USA., pp. 1-9.

Nomura T., et al., "Wireless Passive Strain Sensor Based on Surface Acoustic Wave Devices", Sensors & Transducers journal, Apr. 15, 2008, 90, International Frequency Sensor Association Publishing, 61-71.

PCT/US06/61994 International Search Report and Written Opinion of the International Searching Authority, dated Oct. 17, 2007, 9 pages.

PCT/US08/76123 International Search Report and Written Opinion of the International Search Authority, dated May 19, 2009, 15 pages.

PCT/US08/76123 Partial International Search Report, dated Jan. 12, 2009, 3 pages.

Pohl, et al., "A Review of Wireless SAW Sensors IEEE Transactions on Ultrasonics, Ferroelectrics, and Frequency Control,", Mar. 2000, 47 (2), IEEE, 317-332.

Reindl, et al., "SAW-Based Radio Sensor Systems", IEEE Sensors Journal, Jun. 2001, 1 (1), IEEE, 69-78.

Reindl, et al., "Theory and Application of Passive SAW Radio Transponders as Sensors", IEEE Transactions on Ultrasonics, Ferroelectrics, and Frequency Control, Sep. 1998, 45 (50, 1281-1292.

Scholl G., et al., "SAW-Based Radio Sensor Systems for Short-Range Applications", IEEE Microwave Magazine, Dec. 2003, IEEE., 68-76.

Seibold, Ulrich et al., "A 6-axis force/torque sensor design for haptic feedback in minimally invasive robotic surgery," In: Proceedings of the 2nd VDE World Microtechnologies, 2003, 6 Pages.

Sherrit, et al., "BAW and SAW Sensors for In-Situ Analysis", Proceedings of the SPIE Smart Structures Conference San Diego, CA, Mar. 2-6, 2003, 5050 (11), SPIE, 11 pages.

U.S. Appl. No. 60/755,108, filed Dec. 30, 2005, Blumenkranz, Stephen J. et al.

U.S. Appl. No. 60/755,157, filed Dec. 30, 2005, Larkin, David Q.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wang, et al., "Optimal Design on SAW Sensor for Wireless Pressure Measurement Based on Reflective Delay Line", Sensors and Actuators A: Physical, Sep. 12, 2007, 139 (1-2), Elsevier B.V., pp. 2-6.

* cited by examiner

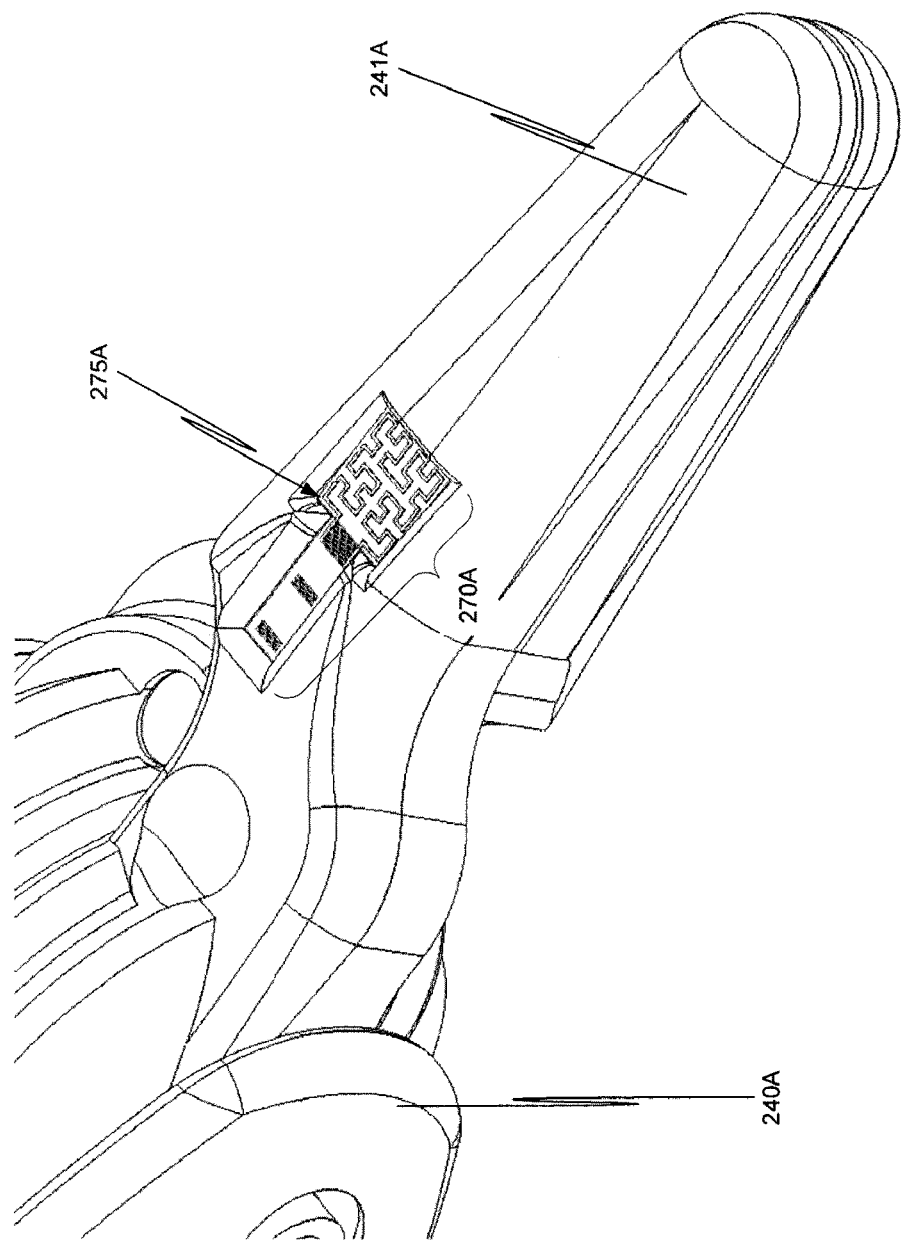

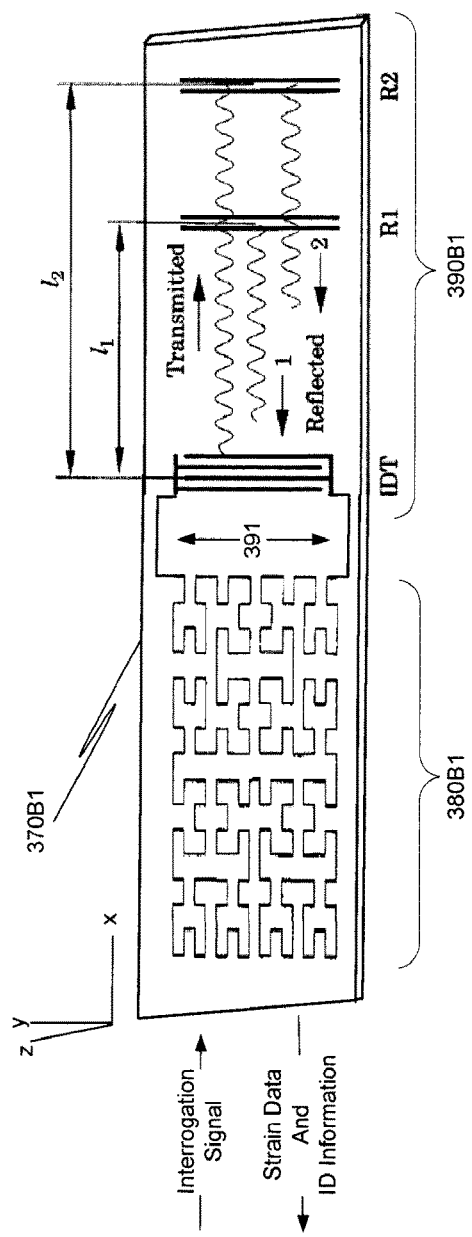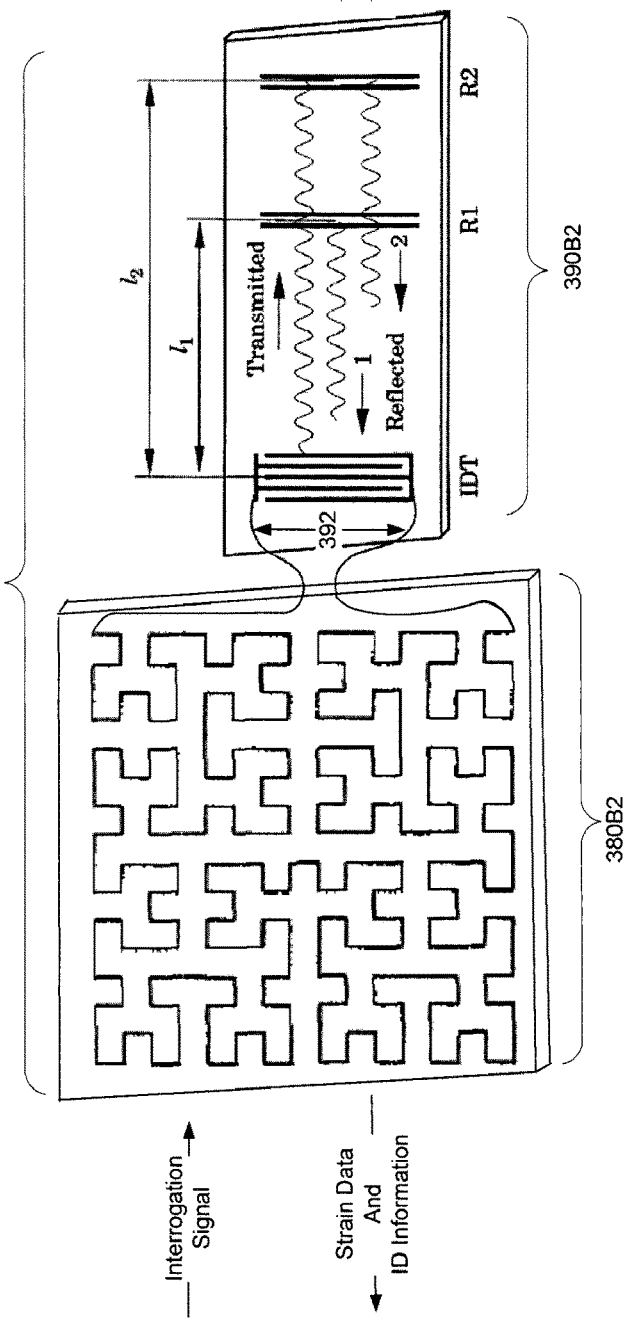

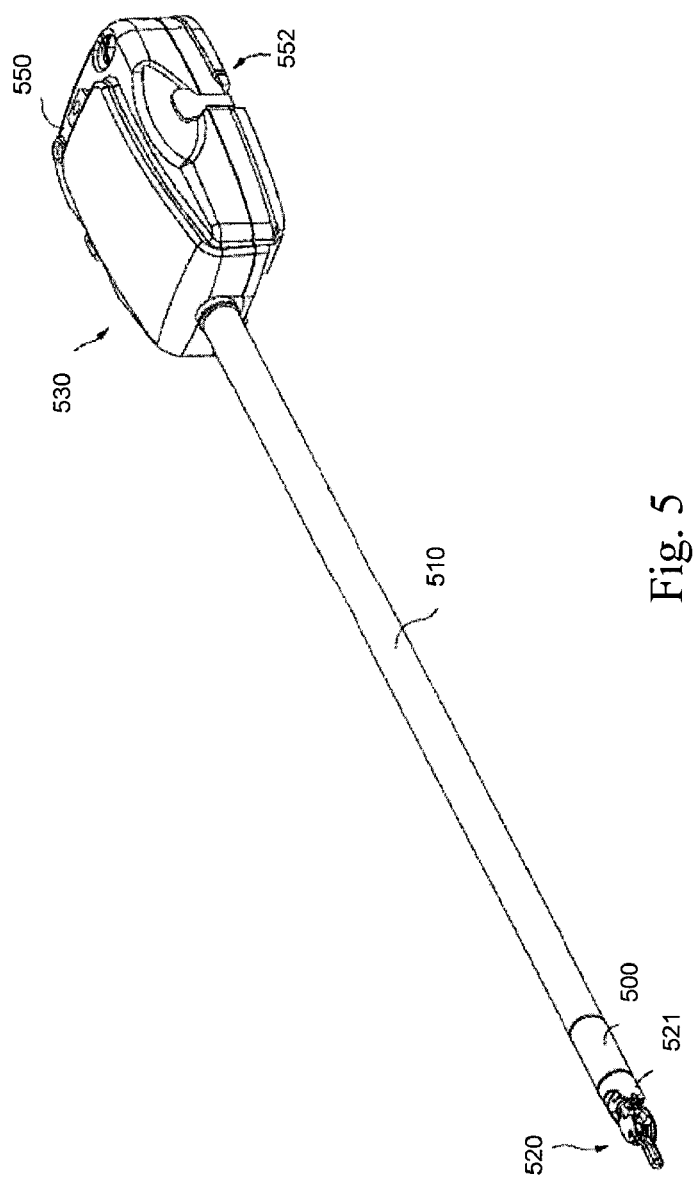

WIRELESS FORCE SENSOR ON A DISTAL PORTION OF A SURGICAL INSTRUMENT AND METHOD

CROSS-REFERENCE TO RELATED APPLICATIONS AND PATENTS

This application is a continuation of U.S. patent application Ser. No. 14/107,692 (filed Dec. 16, 2013), which is a continuation of U.S. patent application Ser. No. 12/634,489 (filed 9 Dec. 2009, now U.S. Pat. No. 8,628,518 B2), which is continuation-in-part of U.S. patent application Ser. No. 11/864,974 (filed Sep. 29, 2007, now U.S. Pat. No. 8,375,808 B2), which is a continuation-in-part of U.S. application Ser. No. 11/537,241 (filed Sep. 29, 2006, now U.S. Pat. No. 8,945,095 B2), which claims priority to and the benefit of U.S. Provisional Application No. 60/755,108 (filed Dec. 30, 2005), all of which are incorporated by reference herein in their entireties for all purposes.

TECHNICAL FIELD

The present invention relates generally to minimally invasive surgical systems, e.g., minimally invasive teleoperated robotic surgical systems, and, more particularly, to an improved apparatus, and method for sensing forces applied by a surgical instrument.

BACKGROUND

In teleoperated robotically assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces, or the like, which are operatively coupled to the surgical instruments through a controller with servo motors for articulating the instruments' position and orientation at the surgical site.

The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves (cannulas) inserted through incisions into a body cavity, such as the patient's abdomen. There are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, dissecting, cauterizing, coagulating tissue, etc. A surgeon may employ a large number of different surgical instruments/tools during a procedure.

This new surgical method through remote manipulation has created many new challenges. One challenge is providing the surgeon with the ability to accurately "feel" the tissue that is being manipulated by the surgical instrument via the robotic manipulator. The surgeon must rely on visual indications of the forces applied by the instruments or sutures.

Various attempts to measure the forces and torques and to provide feedback to a surgeon have been made. One device for this purpose from the laboratory of G. Hirzinger at DLR Institute of Robotics and Mechatronics is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

As described in A. Dalhlen et al., "Force Sensing Laparoscopic Grasper," U. Wisconsin Coll. Eng., Apr. 28, 2006 (http://homepages.cae.wisc.edu/~bme402/grasping_instruments_s06/reports/Final_Paper.pdf), a team at the Univ. of Wisconsin led by A. Dahlen and advised by W. Murphy considered strain gauges on several parts of the jaw actuation mechanism of a manual laparoscopic bowel grasper finally settling on the hand grip. Also, as described at Paragraph 4.2, Medical Robotics, I-Tech Education and Publishing, Vienna, Austria, Pg. 388, (2007) (ISBN 13: 978-3-902613-18-9), U. Seibold et al at the German DLR Institute similarly measured the gripper actuation cable tension to calculate the grip force.

F. van Meer at LAAS/CNRS (2004) in Toulouse France pursued and patented what is described as a MEMS 2D silicon force sensor cemented to the inner surfaces of opposing folded sheet metal jaws of a five millimeter (mm) instrument and connected by ten wires. The sensor is capacitive and requires capacitive readout electronics located nearby. See Van Meer, et al., "2D Silicon Macro-force Sensor For a Tele-operated Surgical Instrument," *Proc. 2004 Int'l Conf. on MEMS, Nano and Smart Systems,* (2004) (ICMENS-04). U.S. Pat. No. 6,594,552 to Nowlin et al. (2003) describes a method of governing grip force without jaw sensors and instead is based on a position control loop of the instrument jaws with the robot master grip command force dependent on springs resisting closure of the master finger levers.

G. Fischer et al., at Johns Hopkins University, (2006) attached strain gauges and blood oxygen sensors with lead wires to the leaves of a fan retractor to measure surgical forces (not grip forces) and resulting ischemia in liver tissue. See Fischer et al, "Ischemia and Force Sensing Surgical Instruments for Augmenting Available Surgeio Information," *ERCCIS-JHU, Int'l Conf. on Biomedical Robotics and Biomechatronics* (BioRob) (February 2006).

E. Dutson et al., at UCLA, (2005) applied wire connected pressure sensing pads to the inner faces of a daVinci robotic surgical instrument and displayed the resulting contact force signal to the surgeon using a pneumatically actuated pad on the robot master finger levers. See Dutson E P, Hwang R, Douraghy A, Mang J, Vijayaraghavan A, Gracia C, Grundfest N, "Haptic feedback system for robotic surgery," *Society of American Gastrointestinal and Endoscopic Surgeons (SAGES) 2005 Annual Meeting,* Ft. Lauderdale, Fla., (Apr. 13-16, 2005).

U.S. Pat. No. 7,300,450 to Petronella et al. (2007) describes a laparoscopic instrument with a jaw force sensor comprising an optic fiber passing into a moveable jaw and aimed a reflecting surface on the jaw so that the amount of light reflected varies with the force on the law.

Each of these methods has shortcomings. For example, gripper jaw actuator cable forces do not measure the effects of jaw pivot friction wk ich rises as the law actuation force increases. Contact sensors applied to the instrument jaw working face are subject to high contact pressures that may damage the sensor. An optic fiber or wires passing through the instrument wrist to a jaw sensor is liable to breakage.

SUMMARY

An apparatus and method improve force feedback to a surgeon performing a minimally invasive surgery such as a minimally invasive teleoperated robotic surgery. A surgical instrument includes a distal portion. A force sensor is operatively mounted on the distal portion. The force sensor includes a wireless package, which wirelessly provides (1) identification information of the surgical instrument and (2) strain data related to the distal portion.

The surgical instrument also includes a wrist joint and a surgical end effector mounted distal to the wrist joint of the surgical instrument. The distal portion is on the surgical end effector in one aspect. In another aspect, the distal portion is proximal to the wrist joint.

In one embodiment, the surgical end effector includes a jaw and the distal portion is on the law. The jaw can be made of an electrically non-conductive material.

The wireless package includes a surface acoustic wave strain sensor with identification information. The surface acoustic wave strain sensor includes identification information of the surgical instrument. The wireless package also includes, in one embodiment, a small folded antenna electrically coupled to the surface acoustic wave strain sensor with identification information. In another embodiment, the antenna is a non-folded antenna.

In one aspect, the small folded antenna and the surface acoustic wave strain sensor have a common surface on a substrate and are electrically connected by one of trace wire connections and bond wire connections. In another aspect, the folded antenna is on a first surface of a substrate and the surface acoustic wave strain sensor is on a second surface of the substrate. The second surface is opposite and removed from the first surface. In yet another aspect, the folded antenna and the surface acoustic wave strain sensor are on different substrates, and are electrically connected.

The identification information includes an identification of a type of surgical instrument. The identification information further includes unique identification of one and only one surgical instrument in the type of surgical instrument.

In another aspect, this surgical instrument is included in an apparatus that also includes an interrogator antenna. The interrogator antenna is configured to transmit wireless interrogation signals to the wireless package, and to receive wireless signals, from the wireless package, containing the strain data and identification information. The apparatus further includes a wireless interrogator, coupled to the interrogator antenna, to provide signals to the interrogator antenna and to receive signals from the interrogator antenna.

In one aspect, the interrogator antenna is located external to a patient undergoing surgery. In another aspect, the interrogator antenna is mounted on another surgical instrument so that when a patient is undergoing surgery, the interrogator antenna is internal to the patient.

The apparatus also includes a computer connected to the wireless interrogator to analyze a signal including (1) identification information of the surgical instrument and (2) strain data from the distal portion, and to convert the strain data into a force signal. The force signal is used to provide feedback to a surgeon operating the surgical instrument.

A method of using the force sensor receives a wireless interrogation signal in a wireless package mounted on a distal portion of a surgical instrument. The method further includes wirelessly transmitting from the wireless package, in response to the interrogation signal, (1) identification information of the surgical instrument and (2) strain data from the distal portion.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 2B to 2D are views of a first aspect of the wireless force sensor of FIG. 2A.

FIG. 3C illustrates a wireless package that includes a small folded antenna and a surface acoustic wave strain sensor with identification information on a common substrate.

FIG. 3D illustrates a wireless package that includes an antenna and a surface acoustic wave strain sensor with identification information in separate packages that are connected together.

FIG. 5 is a perspective view of a surgical instrument including a force sensor apparatus operably coupled proximal (or inboard) to a wrist joint in accordance with an embodiment of the present invention.

Figure 1A:
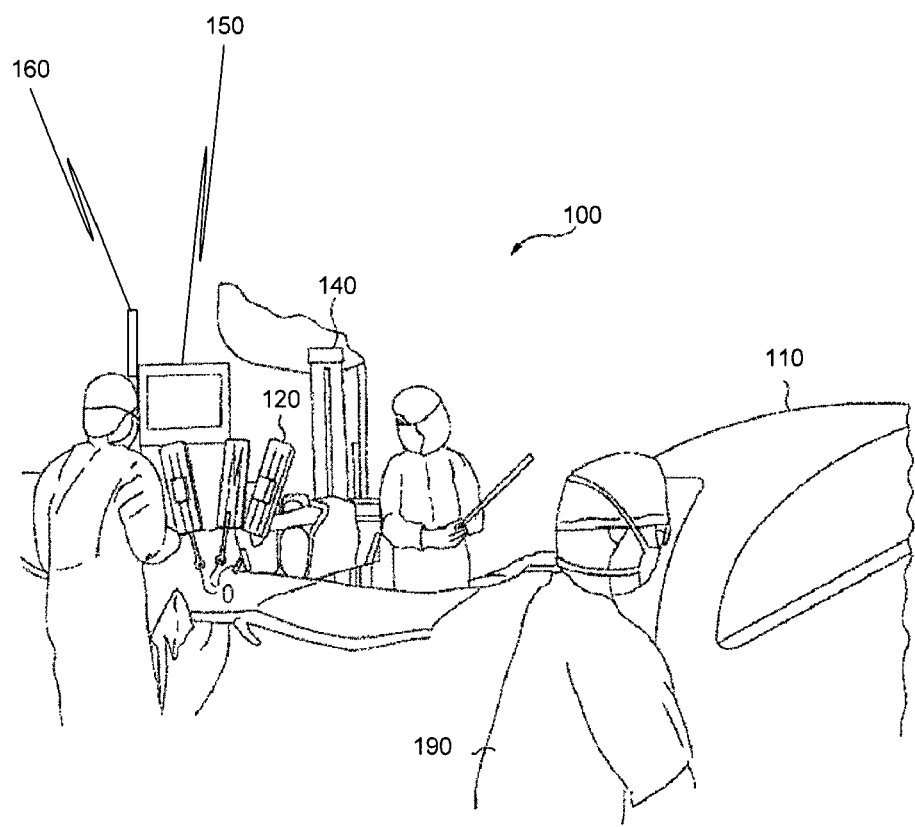
FIG. 1A is a perspective view of a minimally invasive surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be drawn to scale.

DETAILED DESCRIPTION

A multi-component minimally invasive surgical system 100 (FIGS. 1A to 1C), e.g., a teleoperated robotic surgical system, and method sense forces applied to tissue, sutures, needles, clips, and the like via a distal end of a surgical instrument while performing, for example, teleoperated robotically assisted surgical procedures on a patient, particularly including open surgical procedures, neurosurgical procedures, and minimally invasive procedures, such as laparoscopy, arthroscopy, thoracoscopy, and the like. A wireless force sensor 275 (FIG. 2A) mounted on a distal portion of a surgical instrument 230 is particularly useful as part of a minimally invasive surgical system 100 that allows surgeon 190 to manipulate surgical instruments through a servomechanism from a location 110 remote from the patient.

To that end, the combined manipulator apparatus or slave and surgical instrument of the present invention is usually driven by a master having the same degrees of freedom (e.g., three degrees of freedom for position and three degrees of freedom for orientation plus grip) to form a telepresence system with force reflection or other scalar force magnitude display. A description of a suitable slave-master system can be found in U.S. Pat. No. 6,574,355, the complete disclosure of which is incorporated herein by reference for all purposes.

Figure 1B:
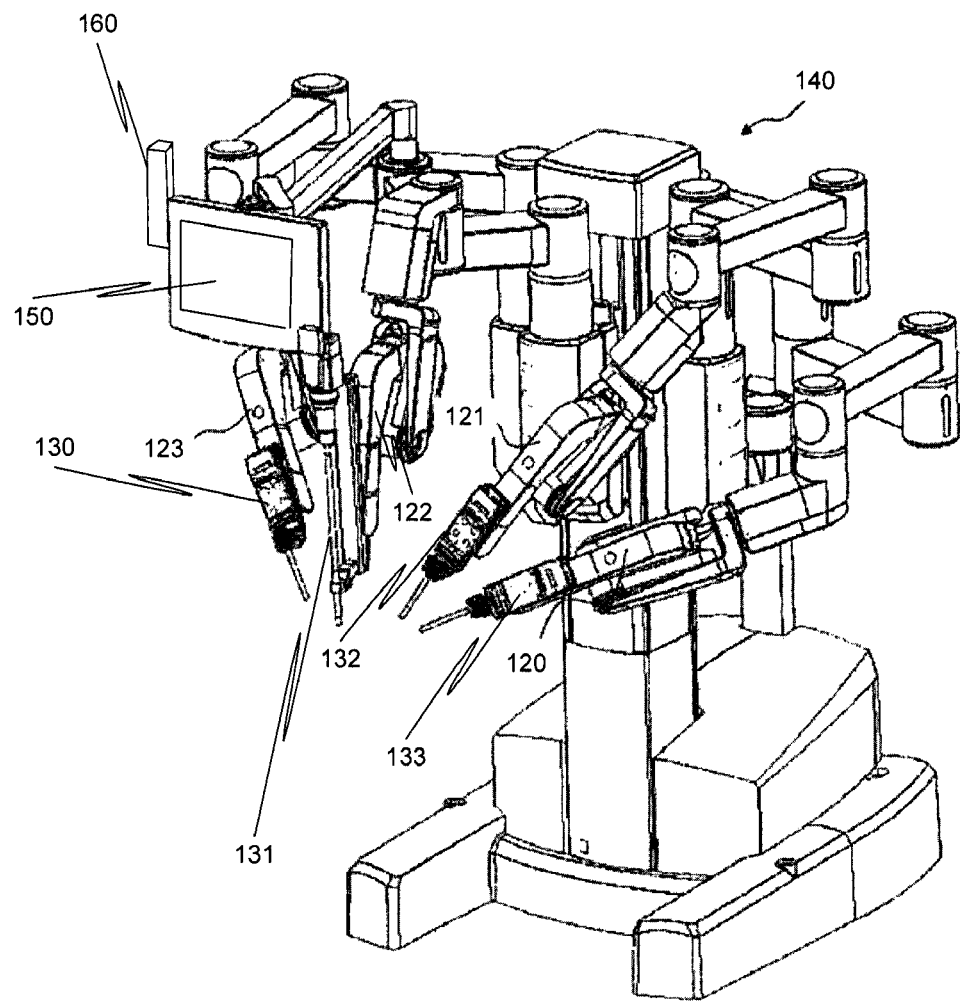
FIG. 1B is a perspective view of a minimally invasive surgical arm cart system of the minimally invasive surgical system in FIG. 1A in accordance with an embodiment of the present invention.
Figure 1C:
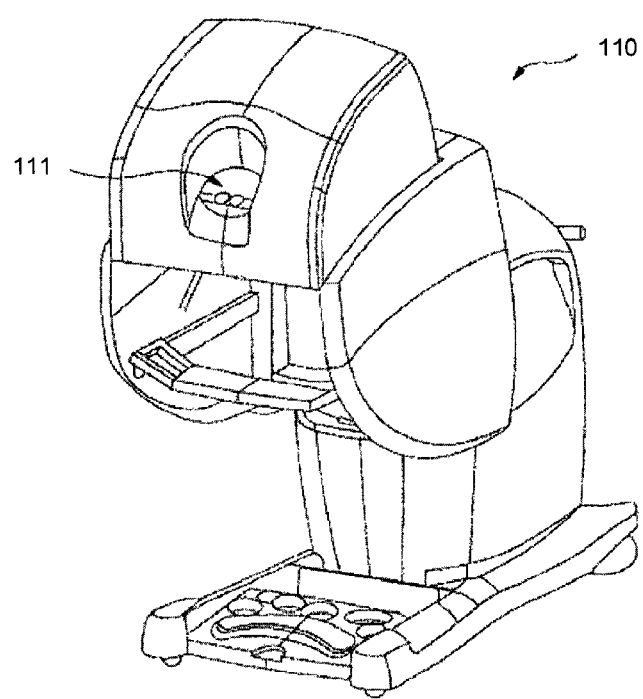
FIG. 1C is a front perspective view of a master console of the minimally invasive surgical system in FIG. 1A in accordance with an embodiment of the present invention.

In FIGS. 1A to 1C, minimally invasive surgical system 100 is illustrated that includes at least one surgical instrument 230 (FIGS. 2A to 2G) having, in one aspect, a wireless force sensor 275, mounted on a distal portion of surgical instrument 230, as described more completely below. In one aspect, the distal portion is proximal to a wrist joint, and in another aspect, the distal portion is distal to the wrist joint. See FIGS. 2A to 2G and FIG. 5.

As explained more completely below, wireless force sensor 275 includes a wireless package, which in response to a received wireless interrogation signal measures strain in the distal portion and wirelessly transmits (1) identification information of surgical instrument 230 (FIGS. 2A to 2G) and (2) strain data from the distal portion to an interrogator antenna in the operating room. In this example, the interrogator antenna is included in a wireless interrogator unit 160 attached to display 150 (FIG. 1A). In one aspect, the strain data is processed to provide real-time force feedback to surgeon 190 in the surgical robot master's finger grips and in another aspect in a display viewed by surgeon 190.

Surgeon 190 using a surgical instrument including wireless force sensor 275 is able to sense, for example, the jaw grip force of various graspers and needle drivers to avoid damaging tissue, sutures or needles. The real-time force feedback also allows surgeon 190 to modulate the grip force to improve execution of various surgical tasks while avoiding these types of damage.

Wireless communication is the transfer of information over a distance without the use of electrical conductors or wires. Similarly, a wireless signal is a signal that travels over the distance of the wireless communication without the use of electrical conductors or wires.

The wireless communication eliminates the prior art need for wires from difficult locations on a surgical instrument. The wireless communication also eliminates the need for additional electrical contacts at the sterile adapter interface. In particular, the need for contacts capable of a sufficiently clean signal for strain sensing is eliminated. Finally, the wireless communication and the operation of wireless force sensor 275 at high frequencies (e.g., GHz) provides immunity to cautery noise without resorting to fiber optic strain sensing which would be significantly more difficult at the jaw location than as presently performed on the instrument shaft.

As shown in FIGS. 1A through 10, minimally invasive surgical system 100 generally includes one or more surgical manipulator assemblies 120 to 123 mounted to or near an operating table and a master control assembly located at a surgeon's console 110 (FIGS. 1A and 1C) for allowing a surgeon to view the surgical site and to control manipulator assemblies 120 to 123. System 100 also includes one or more viewing scope assemblies 131 and a plurality of surgical instrument assemblies adapted for being removably coupled to manipulator assemblies 120 to 123, as discussed in more detail below. Minimally invasive surgical system 100 includes at least two manipulator assemblies and preferably at least three manipulator assemblies. The exact number of manipulator assemblies depends on the surgical procedure and the space constraints near the patient among other factors.

A control assembly may be located at surgeon's console 110, which is usually located in the same room as the operating table so that surgeon 190 may speak to his/her assistant(s) and directly monitor the operating procedure. However, it should be understood that the surgeon 190 can be located in a different room or a completely different building from the patient.

The master control assembly generally includes a support, a monitor for displaying an image of the surgical site to surgeon 190, and one or more master(s) for controlling manipulator assemblies 120 to 123. Master(s) may include a variety of input devices, such as hand-held wrist gimbals, joysticks, gloves, trigger-guns, hand-operated controllers, voice recognition devices, or the like. Preferably, master(s) are provided with the same degrees of freedom as the combined manipulator and surgical instrument assembly. In this aspect, the masters include a capability to provide force feedback based on the wireless strain data from the distal portion of surgical instrument 230.

In conjunction with the endoscopic view, this provides surgeon 190 with telepresence, the perception that the surgeon is immediately adjacent to and immersed in the surgical site, and intuitiveness, the perception that the master(s) are integral with the surgical instruments so that surgeon 190 has a strong sense or directly and intuitively controlling the surgical instruments as if the instruments are part of, or held in his/her hands. Position, force, and tactile feedback sensors (not shown) may also be employed on the surgical instrument assemblies to transmit position, force, and tactile sensations from the surgical instrument back to the surgeon's hands, ears, or eyes as he/she operates minimally invasive surgical system 100. One suitable system and method for providing telepresence to the operator is described in U.S. Pat. No. 6,574,355, which has previously been incorporated herein by reference.

Monitor 111 (FIG. 1C) is suitably coupled to viewing scope assembly 131 such that an image of the surgical site is provided adjacent the surgeon's hands on surgeon console 110. Preferably, monitor 111 displays an image that is oriented so that surgeon 190 feels that he or she is actually looking directly down onto the surgical site. To that end, an image of surgical instruments appears to be located substantially where the surgeon's hands are located. In addition, the real-time image is a stereoscopic image such that the surgeon can manipulate a surgical end effector of a surgical instrument via the hand control as if viewing the workspace in substantially true presence. The image simulates the viewpoint or orientation of a surgeon who is physically manipulating the surgical instrument.

A servo control is provided for transferring the mechanical motion of masters to manipulator assemblies 120 to 123. The servo control may be separate from, or integral with, manipulator assemblies 120 to 123. The servo control provides force feedback and, in some aspects, torque feedback from surgical instruments to the hand-operated masters, in addition, the servo control may include a safety monitoring controller (not shown) to safely halt system operation, or at least inhibit all robot motion, in response to recognized undesirable conditions (e.g., exertion of excessive force on the patient, mismatched encoder readings, etc.).

The servo control preferably has a servo bandwidth with a 3 dB cut off frequency of at least 10 Hz so that the system can quickly and accurately respond to the rapid hand motions used by the surgeon and yet to filter out undesirable surgeon hand tremors. To operate effectively with this system, manipulator assemblies 120 to 123 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2A:
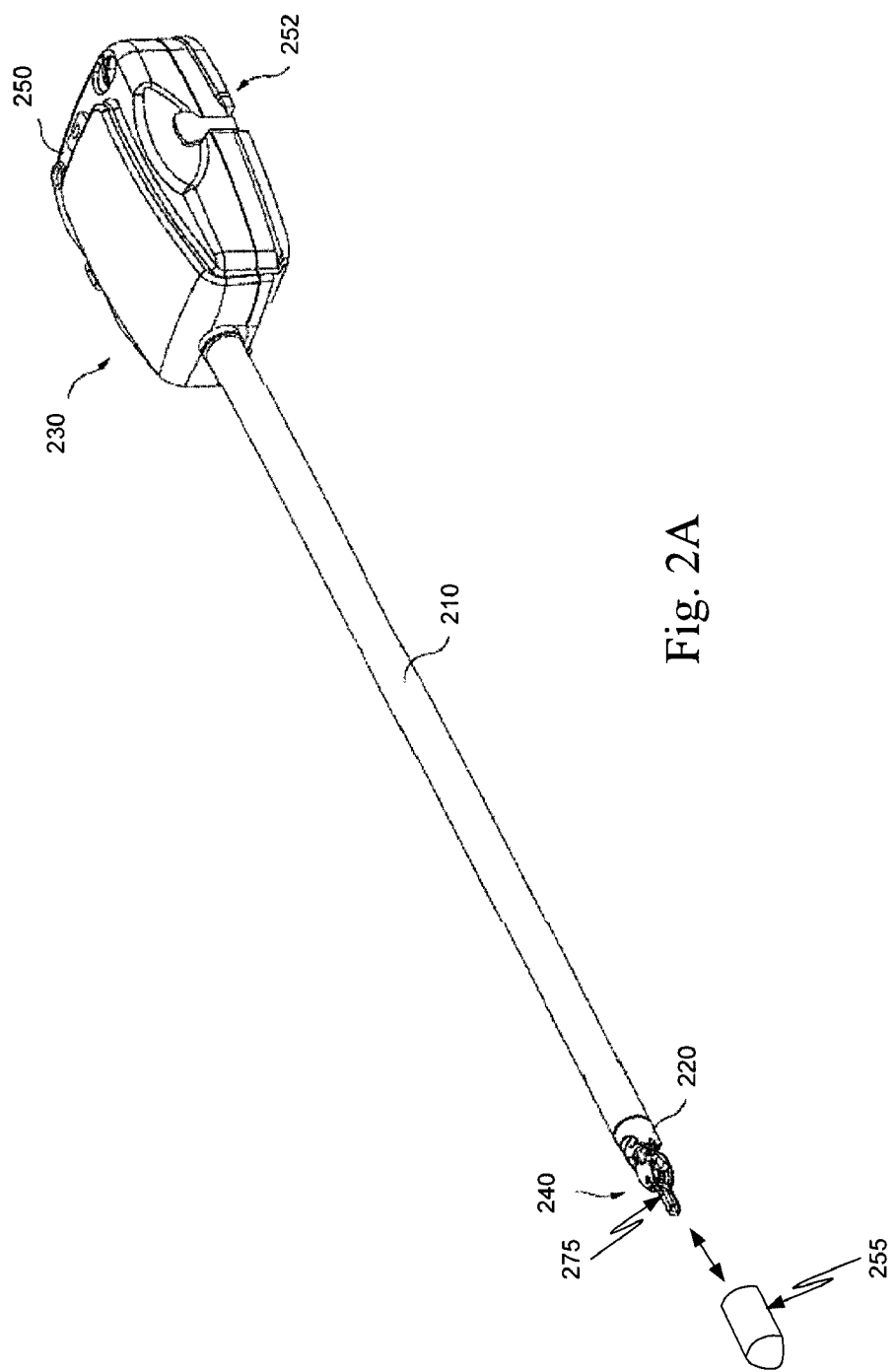
FIG. 2A is a perspective view of a surgical instrument including a wireless force sensor operatively mounted on a distal portion of the surgical instrument in accordance with an embodiment of the present invention.

Referring to FIG. 2A, a perspective view is shown of a surgical instrument 230 including a wireless force sensor 275 operably mounted on distal end portion of a surgical end effector 240. Surgical end effector 240 is coupled to a wrist, joint 220 that in turn is connected to a rigid shaft 210. A housing 250 is operably coupled to a proximal end of rigid shaft 210, and includes a sterile adapter interface 252, which mechanically and electrically couples instrument 230 to any one of manipulator assembly sterile adapters 130, 132, 133. While in this illustration wireless force sensor 275 is distal to wrist joint 220, in some aspects, wireless force sensor 275 can be mounted proximal to wrist joint 220.

Also, in some aspects, when surgical instrument 230 is not in use and is external to the patient, a radio frequency shielded pocket 255 is placed over end effector 240. Radio frequency shielded pocket 255 is constructed and sized so that when pocket 255 is mounted on surgical instrument 230, the radio frequency shielding of pocket 255 shields wireless force sensor 275 from wireless interrogation signals. The temperature stabilization features, described more completely below, may also be incorporated in radio frequency shielded pocket 255.

Applicable housings, sterile adaptor interfaces, and manipulator arms are disclosed in U.S. Patent Application Publication No. 2006/0161138 A1 on Jul. 20, 2006 for U.S. patent application Ser. No. 11/314,040 filed on Dec. 20, 2005, and U.S. Patent Application Publication No. 2007/0137371 A1 on Jun. 21, 2007 for U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

FIGS. 2B to 2G are close-up magnified illustrations of surgical end effector 240, which in this example includes two jaws. Surgical end effector 240 has a range of motion that includes pitch and yaw motion about the x- and y-axes and rotation about the z-axis. These motions as well as actuation of a surgical end effector are provided via cables in housing 250 and cables and/or rods running through shaft 210 and into housing 250 that transfer motion from the manipulator assembly. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

Figure 2B:
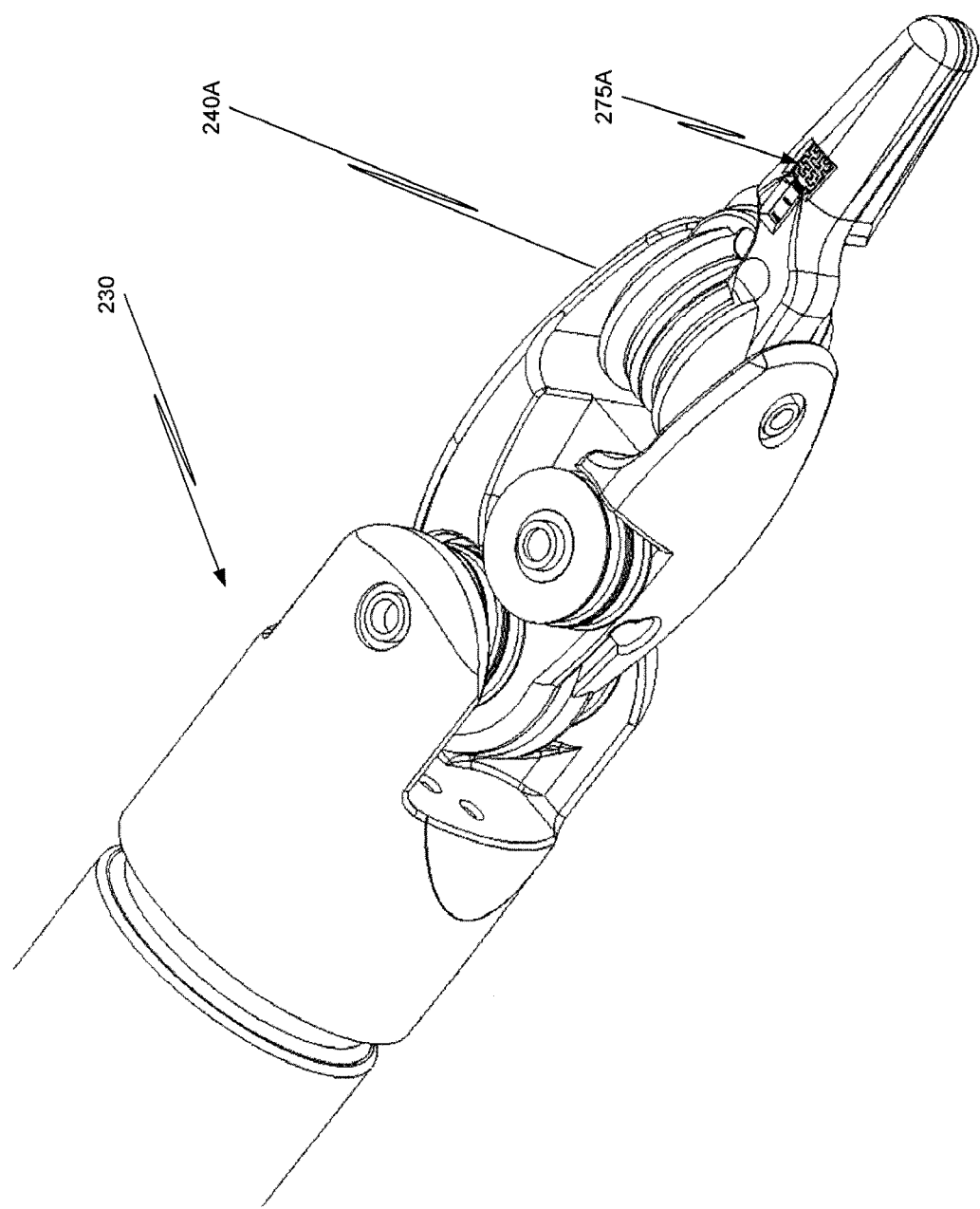
Figure 2D:
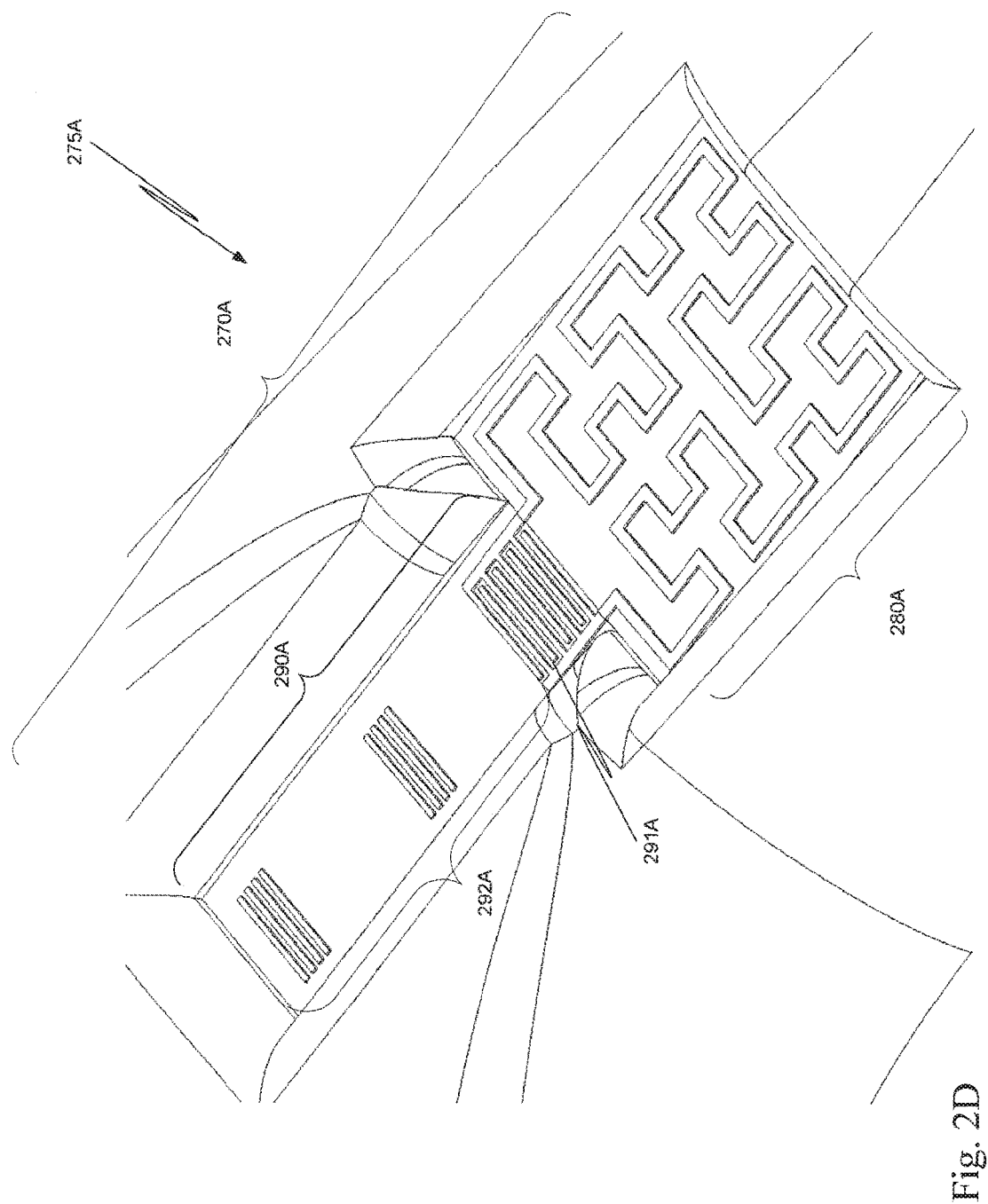

As shown in FIGS. 2B to 2D, wireless force sensor 275A includes a wireless package 270A that is mounted on a distal portion of surgical end effector 240A. As shown in FIGS. 2C and 2D, wireless package 270A is mounted in a recess on a non-contact surface of one jaw 241A of the pair of jaws of surgical end effector 240A. In this aspect, wireless package 270A (FIG. 2D) includes two components, a surface acoustic wave strain sensor with identification information 290A and a small folded antenna 280A. All or part of wireless package 270A may also be mounted on a non-recessed non-contact surface and provided with adequate physical protection.

Figure 2E:
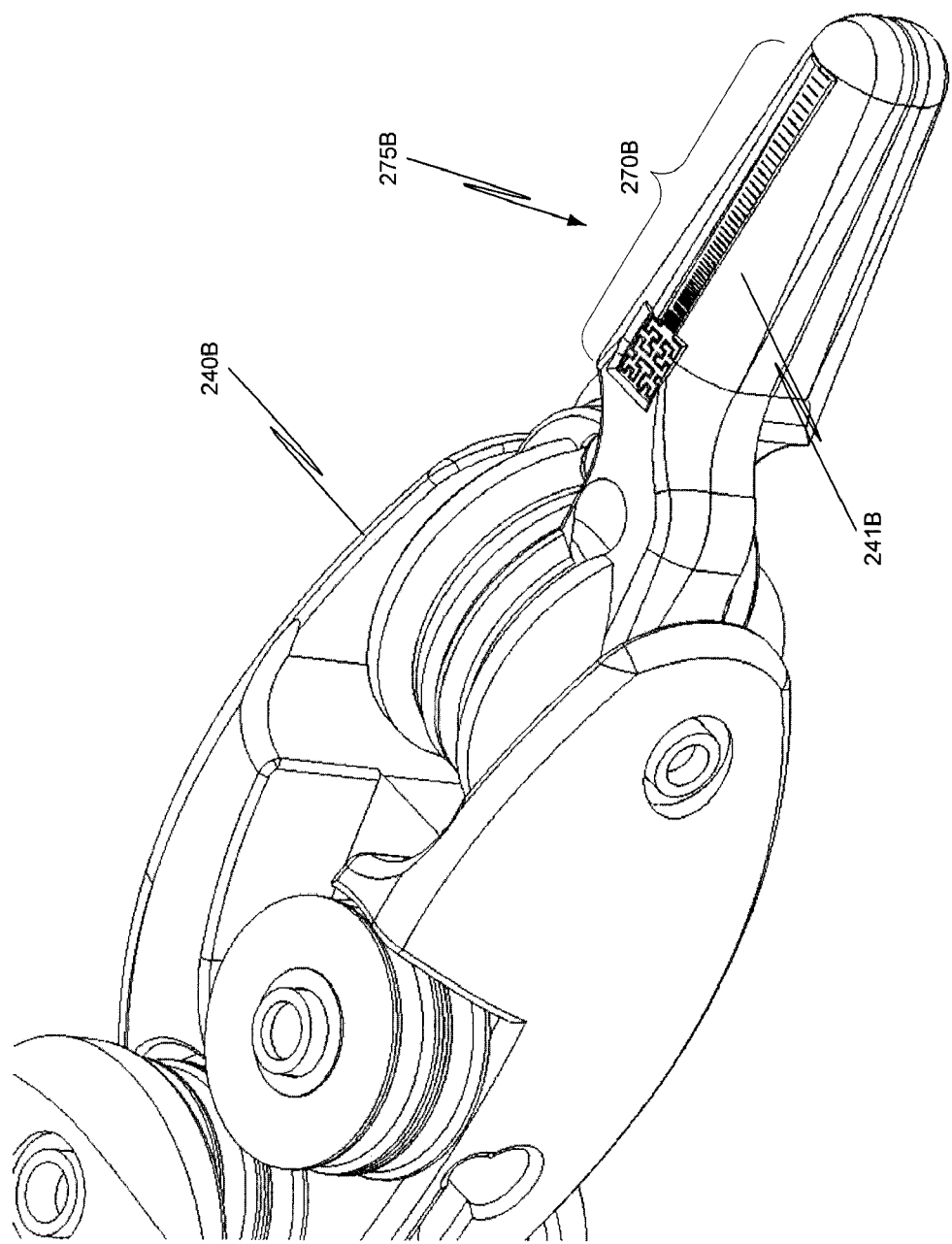
FIG. 2E to 2G are views of a second aspect of the wireless force sensor of FIG. 2A that includes a chirped surface acoustic wave strain sensor with identification information.
Figure 2F:
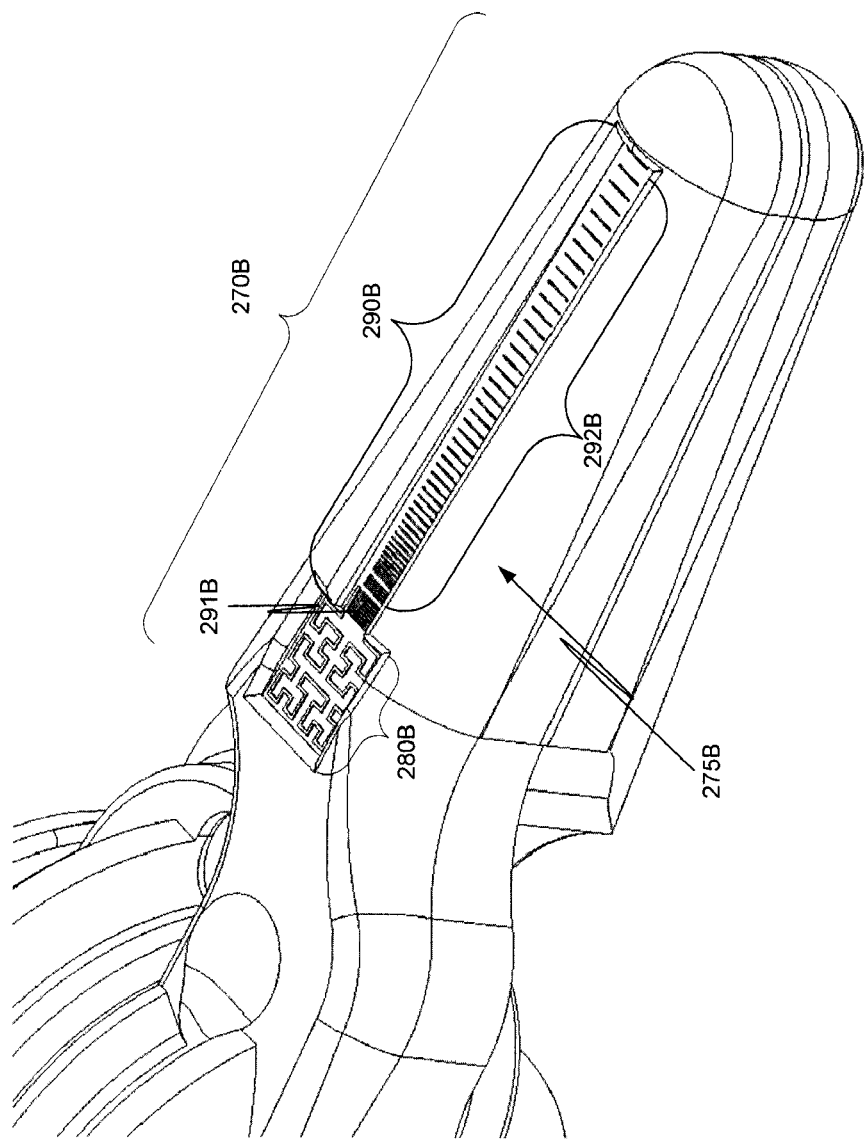
Figure 2G:
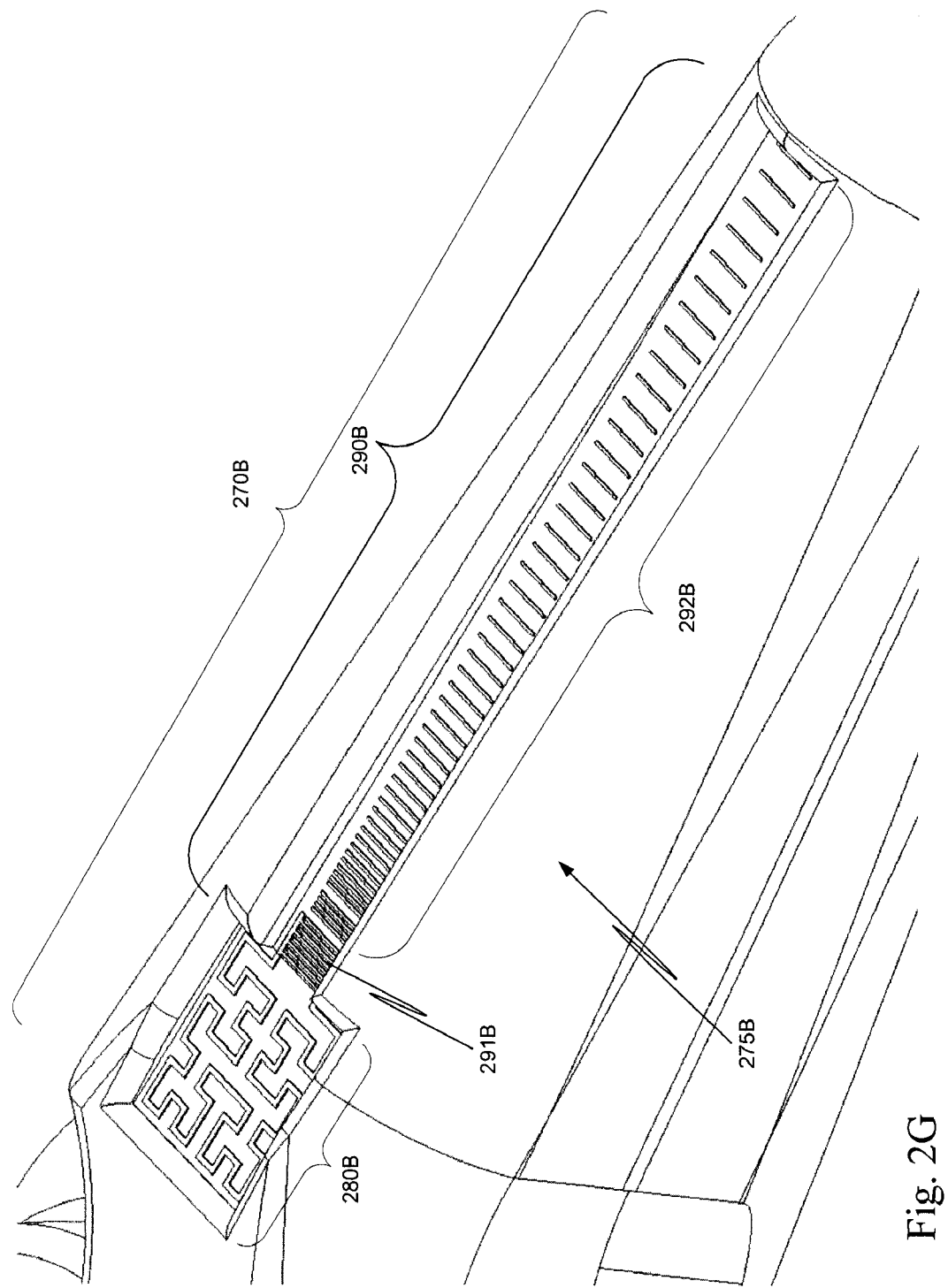

As shown in FIGS. 2E to 2G, wireless force sensor 275B also includes a wireless package 270E that is mounted on a distal portion of surgical end effector 240B. Wireless package 270B is mounted in a recess that extends along the length of a non-contact surface of one jaw 241B of the pair of jaws of surgical end effector 240B. In this aspect, wireless package 270B (FIGS. 2F and 2G) includes two components, a chirped surface acoustic wave strain sensor with identification information 290E and a small folded antenna 280B. All or part of wireless package 270A may also be mounted on a non-recessed non-contact surface and provided with adequate physical protection. As explained more completely below, chirped surface acoustic wave strain sensor 290B allows determination of both the force applied by jaws and the location of that force as well as temperature compensation.

As used herein, a small folded antenna refers to a folded antenna that is of a size that can be mounted on surgical instrument 230 (FIG. 2A) in the vicinity of the surface acoustic wave strain sensor and not interfere with the operation of surgical instrument 230. Examples of small folded antennas include, but are not limited to, a fractal (e.g. Hilbert, Sierpinski, etc.) antenna, a folded antenna designed using genetic algorithms, a crankline antenna, a micro-strip meander antenna, a compact diversity antenna or other minimum size antenna for a given wireless interrogation signal. A non-folded antenna may also be used where space permits as on instrument tube 210 (FIG. 2A), for example.

Surface acoustic wave strain sensor with identification information 290A (FIGS. 20 and 20), 290B (FIGS. 2F and 2G) in turn includes at least an interdigital transducer (IDT) 291A (FIGS. 2C and 2D), 291B (FIGS. 2F and 2G) and a portion 292A, 292B that includes reflectors that provide both strain data and identification information. As is known to those knowledgeable in the field, other components may be used to couple small folded antenna 280A, 280B to surface acoustic wave strain sensor with identification information 290A, 290C. For example, wireless package 270A, 270C can include an impedance matching network, i.e. tuning components such as capacitors and inductors to improve signal coupling to/from wireless interrogator 160 thru antenna 280A, 280C from/to surface acoustic wave strain sensor 290A, 290C.

In one aspect, a wireless interrogation signal, e.g., a 2.4 GHz signal, emitted from interrogation unit 160 (FIG. 1A), is received by antenna 280A (FIG. 29) and/or antenna 280B (FIG. 2G). In the following description, the embodiment of FIGS. 2B to 2D is used, but the description is also applicable to the embodiment of FIGS. 2E to 2G. In response to the wireless interrogation signal, antenna 280A supplies an electrical signal to interdigital transducer (IDT) 291A. Interdigital transducer 291A transforms the received signal into a surface acoustic wave (SAW). The surface acoustic wave propagates along the substrate from interdigital transducer 291A towards the reflectors. Each reflector reflects part of the incoming surface acoustic wave. The reflectors are placed in a specific pattern so that the reflected waves provide the identification information and provide strain data. Thus, the strain sensors are sometimes referred to as surface acoustic wave strain sensors with identification information. The identification information is effectively encoded in the reflector positioning. The number of reflectors shown herein is illustrative only and is not intended to be limiting to the particular configuration illustrated.

The reflected surface acoustic waves are received by interdigital transducer 291A and are converted back into an electrical signal that is applied to antenna 280A. Antenna 280A radiates a wireless response signal back to interrogation unit 160. The wireless response signal includes strain data and identification information of surgical instrument 230.

Various implementations of wireless packages 270A, 270B and the strain and information reflectors in a surface acoustic wave strain sensor can be utilized. Each of the embodiments discussed more completely below is illustrative only and is not intended to be limiting to the particular aspects presented. In view of these examples, those knowledgeable in the field can implement combinations other than those shown to facilitate use of at least one wireless force sensor on a minimally invasive surgical instrument.

Figure 3A:
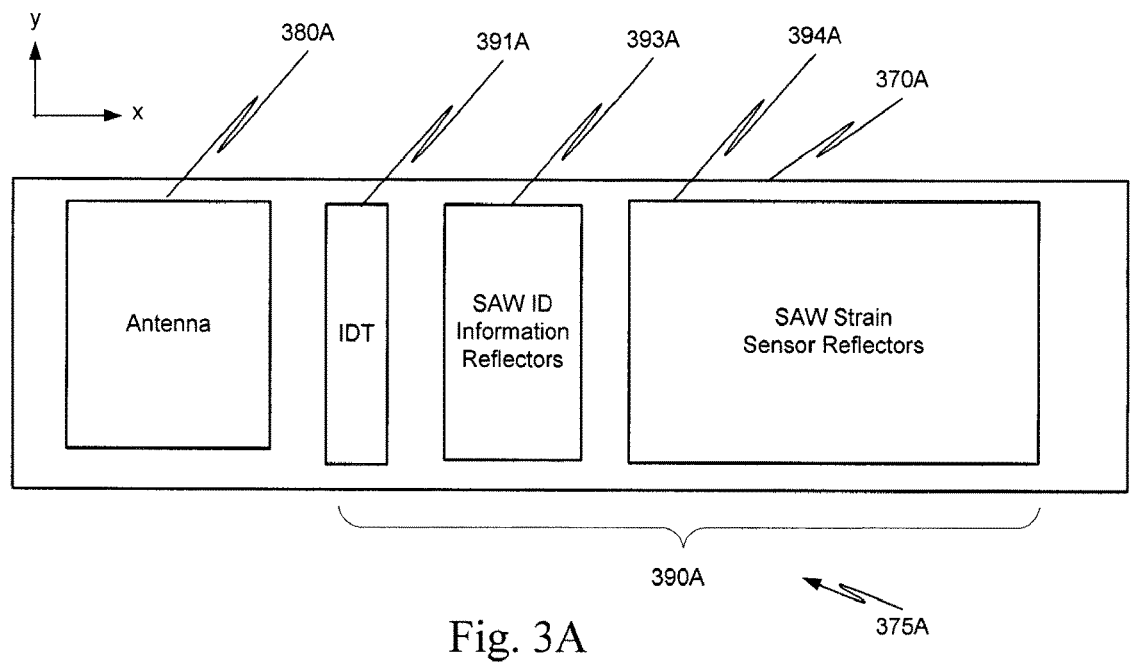
FIG. 3A is a block diagram of one aspect of a force sensor that includes a wireless package, which wirelessly provides (1) identification information of a surgical instrument and (2) strain data.

FIG. 3A is a block diagram of one aspect of a wireless force sensor 375A that includes a wireless package 370A, which wirelessly provides (1) identification information of a surgical instrument and (2) strain data. Wireless package 370A is an integrated package that includes a small folded antenna 380A and a surface acoustic wave strain sensor with identification information 390A. Surface acoustic wave strain sensor with identification information 390A, in turn, includes at least an interdigital transducer 391A, surface acoustic wave identification (ID) information reflectors 393A and surface acoustic wave strain sensor reflectors 394A. Strain sensor 390A could also include an impedance matching network, as described above.

Surface acoustic wave identification (ID) information reflectors 393A generate reflected waves representing the identification information of the surgical instrument on which wireless package 370A is mounted. Surface acoustic wave strain sensor reflectors 394A generate reflected waves representing strain data from the distal portion of the surgical instrument on which surface acoustic wave strain sensor 390A is mounted.

The relative locations of reflectors 393A and 394A are illustrative only and are not intended to be limiting to these specific locations. For example, reflectors 393A could be positioned after reflectors 394A instead of before reflectors 394A as shown in FIG. 3A. Also, in place of reflectors 393A and 394A being arranged serially in a line along an x-axis as shown in FIG. 3A, the two sets of reflectors could be arranged in a stacked configuration (e.g., in two or more parallel rows) along the y-axis. The particular orientation is not essential so long as both identification information and strain data can be generated.

Figure 3B:
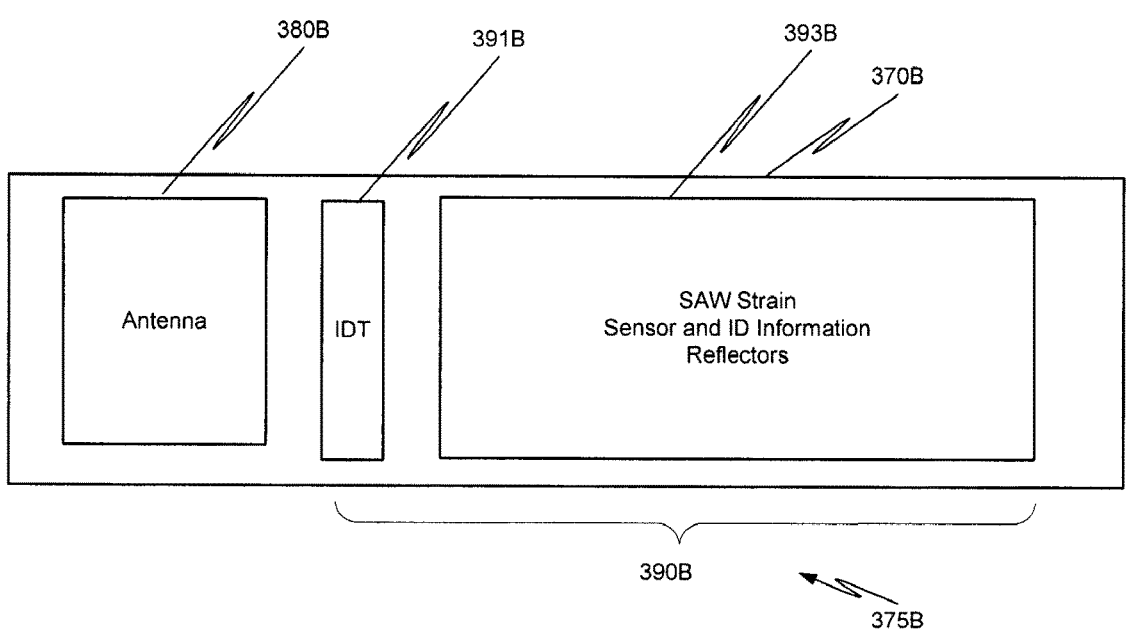
FIG. 3B is a block diagram of another aspect of a force sensor that includes a wireless package, which wirelessly provides (1) identification information of a surgical instrument and (2) strain data.

Also, it is not necessary to use two distinct sets of reflectors. A single set of reflectors can generate both identification information and strain data. For example, FIG. 3B is a block diagram of another aspect of a wireless force sensor 375B that includes a wireless package 375B, which wirelessly provides (1) identification information of a surgical instrument and (2) strain data. Wireless package 370B includes a small folded antenna 380E and a surface acoustic wave strain sensor with identification information 390B. Surface acoustic wave strain sensor with identification information 390B, in turn, includes at least an interdigital transducer 391B, and surface acoustic wave identification (ID) information and surface acoustic wave strain sensor reflectors 393B. The spacing between the reflectors is used to obtain both the strain data and the identification information. Strain sensor 390B could also include an impedance matching network, as described above.

The location of reflectors 393B is illustrative only and is not intended to be limiting to the specific location illustrated. For example, in place of reflectors 393B being placed serially in a line along an x-axis as shown in FIG. 3B, the reflectors could be arranged in a stacked configuration (e.g., in two or more parallel rows) along the y-axis. The particular orientation is not essential so long as both identification information and strain data can be generated.

FIGS. 3C, 3D, 3E and 3F, and 3G illustrate different implementations of wireless package 370B. Similar implementations could be provided for wireless package 370A.

In FIG. 3C, wireless package 370B is implemented as a wireless package 370B1. In wireless package 370B1, small folded antenna 380B1 and surface acoustic wave strain sensor with identification information 390B1 have a common surface on a common substrate in wireless package 370B1, and are arranged serially along an x-axis. Small folded antenna 380B1 is electrically connected to surface acoustic wave strain sensor with identification information 390B1 by traces 391. Alternatively, the electrical connection can be made with bond wire.

Strain sensor 390B1 includes an interdigital transducer IDT, and reflectors R1, R2. Reflector R1 is located a distance $l_1$ from interdigital transducer IDT. Reflector R2 is located a distance $l_2$ from interdigital transducer IDT. The transmitted surface acoustic wave is reflected first by reflector R1 and later by reflector R2. Changes in strain change the characteristics of the reflected surface acoustic waves. This change in characteristics of these waves is the strain data and the strain data can be analyzed to provide force information.

The number and location of the reflectors in strain sensor 390B1 is illustrative only. Also, small folded antenna 380B1 is illustrated as a closed loop antenna. This also is only illustrative and for example, a folded or a straight dipole antenna might be used. Further, the serial arrangement of antenna 380B1 and strain sensor 390B1 along an axis is also only illustrative. Small folded antenna 380B1 might be positioned on any side of strain sensor 390B1, or on multiple sides of strain sensor 390B1 to have a common surface on the common substrate.

In another aspect, as illustrated in FIG. 3D, wireless package 370B is implemented as wireless package 370B2. Small folded antenna 380B2 and surface acoustic wave strain sensor with identification information 390B2 are in separate sub-packages that are electrically connected to form wireless package 370B2. Thus, small folded antenna 380B2 and surface acoustic wave strain sensor with identification information 390B2 are on separate and distinct substrates. Small folded antenna 380B2 is connected to strain sensor 390B2 by electrical wires 392. In one example, electrical wires 392 are a coaxial cable similar to the coaxial cable used in an ultrasound transducer.

Wireless package 370B2 can be used, for example, when small folded antenna 380B2 is too large to be mounted on the same distal portion of the surgical instrument as strain sensor 390B2. For example, strain sensor 390B2 could be mounted distal to wrist 220 (FIG. 2A), while antenna 380B2 is mounted proximal to wrist 220. Also, the sub-package containing small folded antenna 380B may be mounted separately on another more proximal part of the jaw or on the larger wrist clevis surface since the surface area on the clevis side faces is more suitable for a small folded antenna that may need to be larger than strain sensor 390B2.

Strain sensor 390B2 also includes an interdigital transducer IDT, and reflectors R1, R2. Reflector R1 is located a distance $l_1$ from interdigital transducer IDT. Reflector R2 is located a distance $l_2$ from interdigital transducer IDT. The operation of strain sensor 390B2 is similar to that described above for strain sensor 390B1. The number and location of the reflectors in strain sensor 390B2 is illustrative only.

Again, small folded antenna 380B2 is illustrated as a closed loop antenna. This also is only illustrative and for example, a folded or non-folded dipole antenna might be used.

Figure 3E:
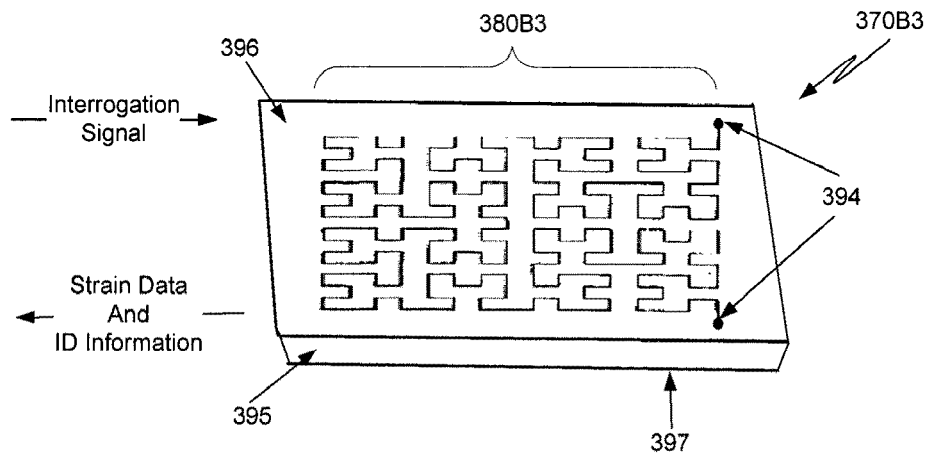
FIG. 3E illustrates a top view of a wireless package that includes a small folded antenna and a surface acoustic wave strain sensor with identification information with the small folded antenna on a first surface of a common substrate.
Figure 3F:
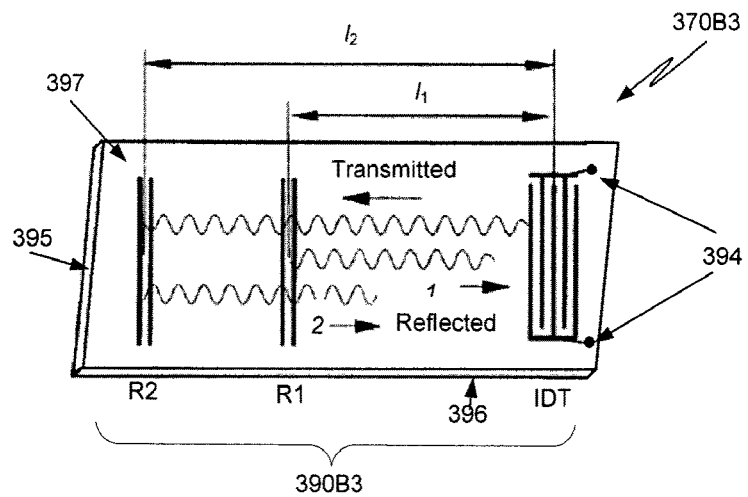
FIG. 3F illustrates a bottom view of a wireless package that includes a small folded antenna and a surface acoustic wave strain sensor with identification information with the strain sensor on a second surface of the common substrate.

In FIGS. 3E and 3F, wireless package 370B is implemented as a wireless package 370B3. FIG. 3E is a top view of wireless package 370B3 and FIG. 3F is a bottom view of wireless package 370B3.

In wireless package 370B3, small folded antenna 380B3 (FIG. 3E) and surface acoustic wave strain sensor with identification information 390B3 (FIG. 3F) are on different surfaces of a common substrate in wireless package 370B3. For example, small folded antenna 380B3 (FIG. 3E) is on a first surface 396 of substrate 395, while surface acoustic wave strain sensor with identification information 390B3 (FIG. 3F) is on a second surface 397 of substrate 395. First surface 396 is opposite and removed from second surface 397. Small folded antenna 380B3 is connected to surface acoustic wave strain sensor with identification information 390B3 by vias 394. In another aspect, antenna 380B3 and strain sensor 390B3 may be on separate substrates, which are then laminated together as a stack having the two opposed surfaces.

Strain sensor 390B3 includes an interdigital transducer IDT, and reflectors R1, R2. Reflector R1 is located a distance $l_1$ from interdigital transducer IDT. Reflector R2 is located a distance $l_2$ from interdigital transducer IDT. The operation of strain sensor 390B3 is similar to that described above for strain sensor 390B1

The number and location of the reflectors in strain sensor 390B3 is illustrative only. Also, small folded antenna 380B3 is illustrated as a closed loop antenna. This also is only illustrative and for example, a dipole antenna might be used.

Figure 3G:
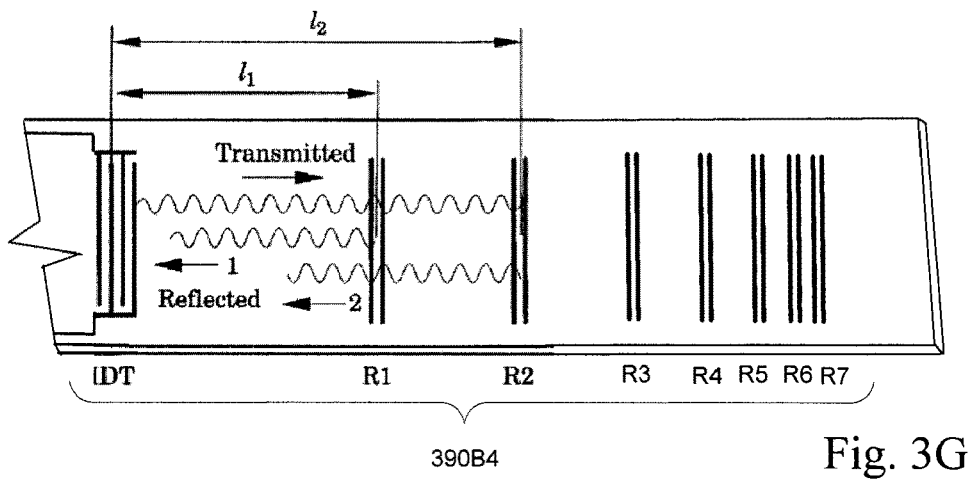
FIG. 3G illustrates a chirped surface acoustic wave strain sensor with identification information for a wireless package.

FIG. 3G is an illustration of an implementation 390B4 of surface acoustic wave strain sensor with identification information 390B (FIG. 3B). Surface acoustic wave strain sensor with identification information 390B4 is a chirped surface acoustic wave strain sensor with identification information and can be included in any of the wireless packages described herein.

Strain sensor 390B4 includes an interdigital transducer IDT, and reflectors R1 to R7. Reflector R1 is located a distance $l_2$ from interdigital transducer IDT. Reflector R2 is located a distance $l_2$ from interdigital transducer IDT. The distance between each pair of reflectors as you move away from interdigital transducer IDT decreases in this example. For example, the distance between reflectors (R1, R2) is greater than the distance between reflectors (R2, R3) and so forth. Alternatively, the distance between each pair of reflectors moving away from interdigital transducer IDT could increase.

As an example, consider that sensor 390B4 is mounted on a needle driver and a needle is grasped in the vicinity of reflector R2. The force applied by the needle driver on the needle will change the shape of the law with respect to reflectors R1 to R2 and so change the distances between these reflectors. However, the distances between reflectors R3 to R7 are not changed. Thus, the strain data represented by the waves reflected by each of reflectors R1 to R7 can be analyzed not only to determine the force applied but also to determine the location of that force based on where the distance change between reflectors stopped.

As indicated above, the small folded antenna used in any of the wireless packages of FIGS. 3A to 3G can be a fractal (e.g. Hilbert, Sierpinski, etc.) antenna, a folded antenna designed using genetic algorithms, a crankline antenna, a micro-strip meander antenna, a compact diversity antenna or other minimum size antenna for a given wireless interrogation signal. The particular antenna selected depends in part on whether a broad-band or narrow-band antenna is needed. A loop or dipole form of these antennas may be used. Where space permits, a non-folded antenna may be used.

As an example, one commercially available 2.4 GHz fractal monopole antenna chip has a size of 3.7 mm by 2 mm, another has a size of 6.7 mm by 6.7 mm by 1 mm, and yet another has a size of 7 mm by 3 mm by 1 mm. Such antennas are available from Fractal. Antenna Systems, Inc., 130 Third Ave., Waltham, Mass., U.S.A, and also from Fractus, S. A., Avda, Alcalde Barnils, 64-68. Sant Cugat del Vallés, 08174 Barcelona, Spain.

A particular antenna is chosen based upon the wireless interrogation signal selected, the size of the antenna needed for the received and transmitted signals, and the antenna properties including gain, impedance, directionality and the like. Also, the substrate characteristics, if appropriate, and the mounting of a particular antenna are chosen to satisfy any ground plane requirements of that antenna. If a particular antenna is not compatible with metal jaws, electrically non-conductive jaws, e.g., ceramic jaws, are utilized in the surgical end effector. For example, ceramic jaws could be made of any one of silicon nitride (SiN) and zirconia.

The selection of the frequency or frequency bandwidth of the wireless interrogation signal is based upon several factors. In one aspect, the frequency or frequency bandwidth of the selected wireless interrogation signal is above the upper harmonics of electro-cautery noise interference. The selected frequency or frequency bandwidth of the wireless interrogation signal functions with a surface acoustic wave strain sensor and small folded antenna that have dimensions suitable for mounting the wireless package in, which these elements are contained on a distal portion of a surgical end effector. The selected frequency or frequency bandwidth of the wireless interrogation signal is compatible with other surgical and patient monitoring equipment used in the operating room. In one aspect, the selected frequency or frequency bandwidth of the wireless interrogation signal has adequate signal strength after penetrating through human tissue. In another aspect, the need to penetrate human tissue is relaxed, as described more completely below.

Each of the surface acoustic wave strain sensors with identification information in FIGS. 3A to 3G includes a piezoelectric substrate. In one aspect, the piezoelectric substrate is selected from Quartz, Lithium Niobate, Lithum Tantalate, Lithium Tetraborate, Gallium Orthophospate, Lead Zirconate Titanate (PZT), Polyvinylidene Fluoride, and the LGX family of crystals including Langasite, Langanite and Langatate. This list of substrate materials is illustrative only and is not intended to be limiting as other substrates that exhibit the piezoelectric effect might be used.

Surface acoustic devices have been reported that included up to 96 bits of identification information. In this aspect, at least enough bits of identification information are provided by the reflectors in the strain sensor to identify the type of the surgical instrument on which wireless force sensor 275 is mounted. In a further aspect, additional reflectors are included to provide unique identification information to uniquely identify the specific surgical instrument within the type, e.g., provide a serial number of the specific surgical instrument. As used herein, unique means that there is one and only one surgical instrument with that identification information.

In one aspect, the surface acoustic wave strain sensor includes reflectors to provide 32 bits of identification information. The 32 bits of identification information are sufficient to provide a unique identity for up to $2^{32}$ different surgical instruments, i.e., $4.3 \times 10^9$ different surgical instruments. The particular number of bits used for the identification information in the strain sensor is not critical so long as each surgical instrument of interest can be assigned a unique identifier.

In some aspects, other identification information may be used in generating the unique identifier of the surgical instrument. For example, some surgical instruments include a non-volatile memory that stores information that can be used, for example, to identify the type of surgical instrument. For such a surgical instrument, the combination of the identification information from the non-volatile memory and the identification information from the surface acoustic wave strain sensor can be combined to associate the strain information with the surgical instrument attached to a manipulator arm and correctly direct force information to a surgeon using that surgical instrument.

Irrespective of the configuration of the wireless package containing the surface acoustic wave strain sensor with identification information and the small folded antenna, the wireless force sensor eliminates the need to route wires through difficult locations on the surgical instrument. In addition, since it is unnecessary to route wires to the force sensor, there is no need for additional electrical contacts at the sterile adapter interface, as described above.

Figure 4A:
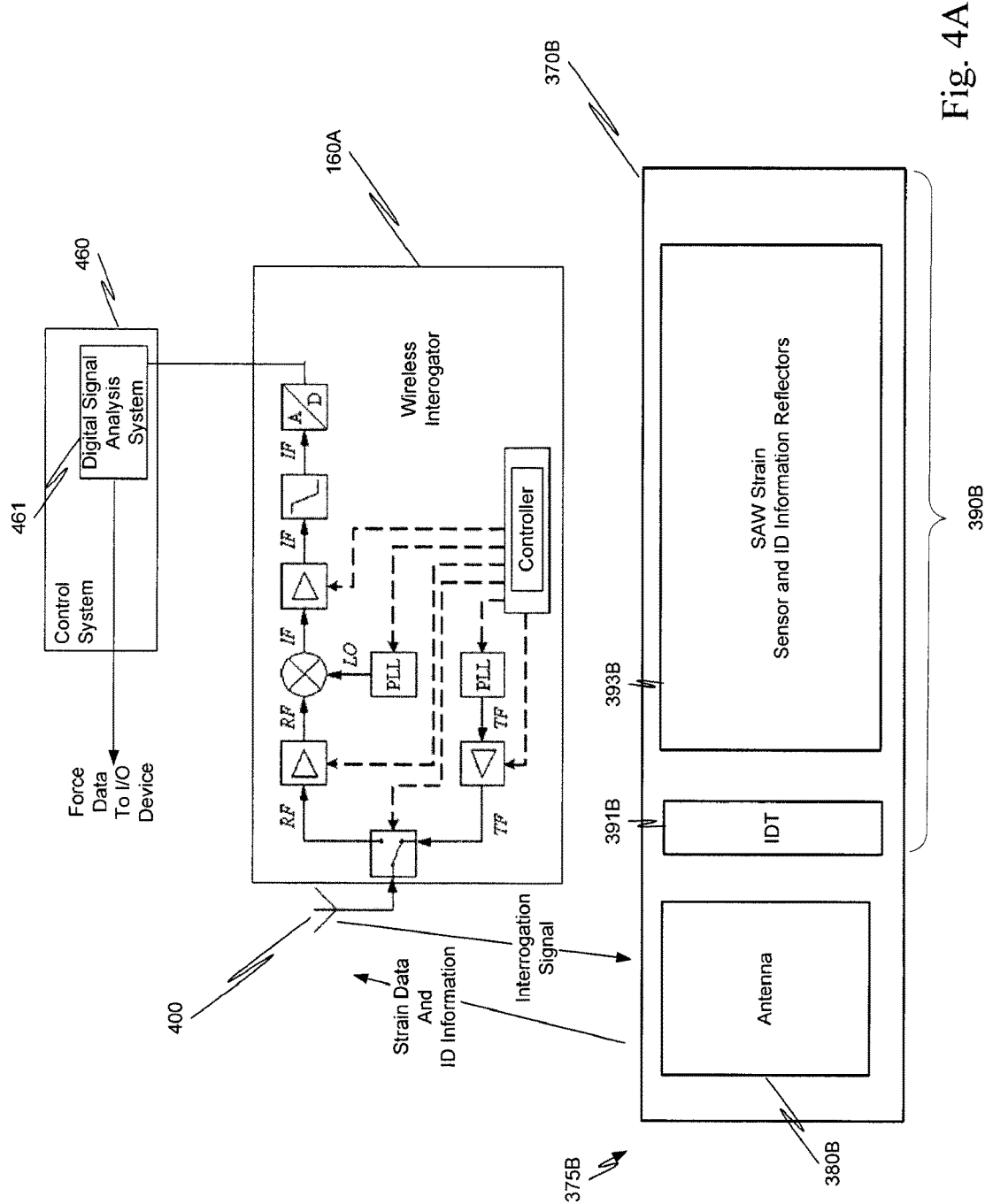
FIG. 4A is a more detailed block diagram of aspects of a minimally invasive surgical system that includes a wireless force sensor and an interrogator antenna, external to a patient, to provide a wireless interrogation signal.
Figure 4B:
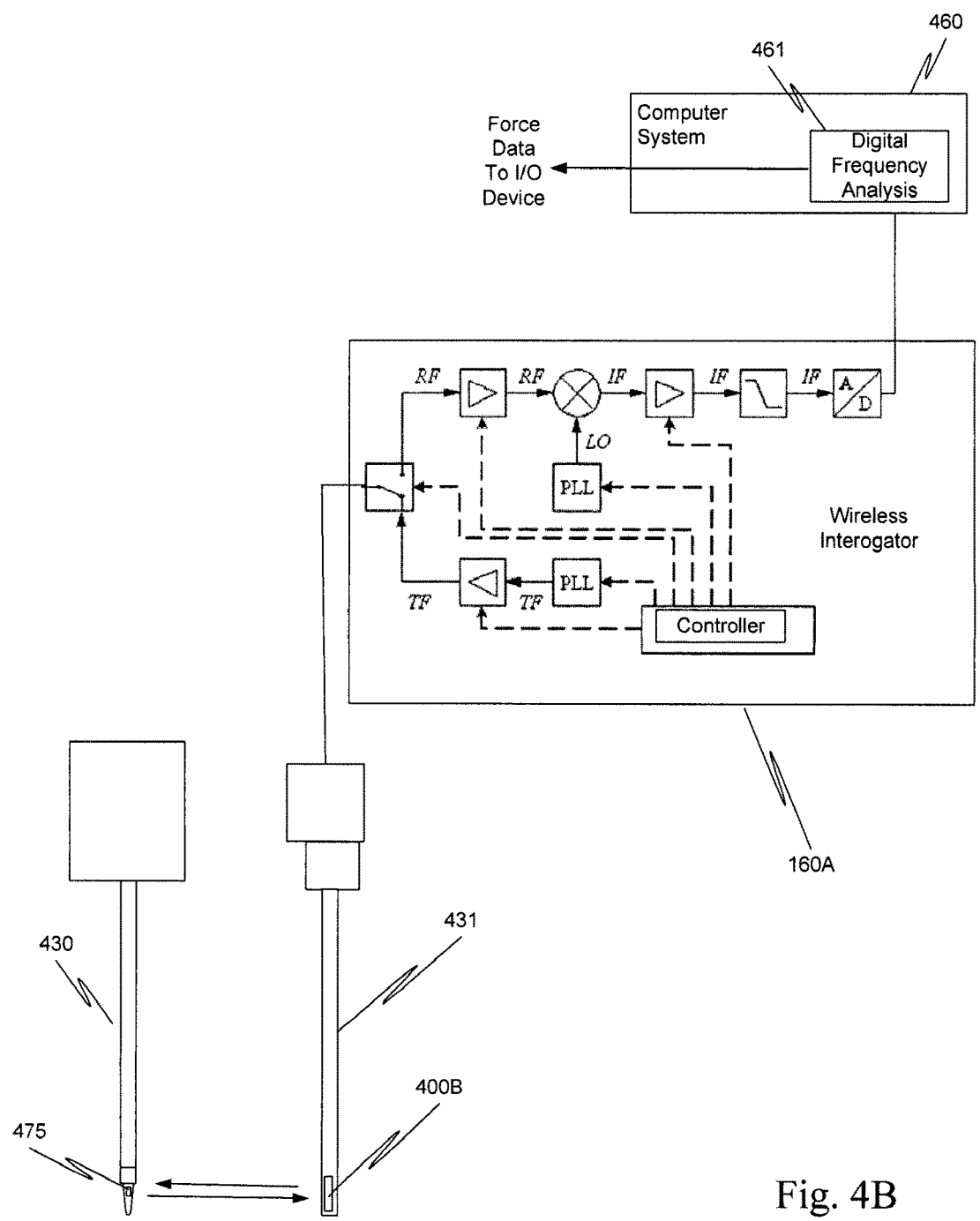
FIG. 4B is a more detailed block diagram of aspects of a minimally invasive surgical system that includes a wireless force sensor and an interrogator antenna, mounted on another minimally invasive surgical instrument, to provide a wireless interrogation signal internal to a patient.

FIG. 4A is a more detailed block diagram of aspects of an apparatus that supports a wireless force sensor 375B mounted on a surgical instrument. The apparatus of FIG. 4A can be used with any of the wireless force sensors described herein.

Wireless package 370B of wireless force sensor 375B is mounted on a distal portion of a surgical instrument, as described above. A conventional wireless interrogator 160A is connected to an interrogator antenna 400 that sends a wireless interrogation signal to wireless package 370B at transmission frequency TF. Wireless interrogator 160A then switches to receive the wireless strain data and identification information signal transmitted from wireless package 370B via antenna 380B. Wireless interrogator 160A processes received radio frequency signal RF and provides a digital signal to digital signal analysis system 461 in control system 460 that in turn is in a control computer.

A processor, e.g., a digital signal processor, in control system 460 performs an analysis of the digital signal to generate strain information, to generate the unique identification, and to use the strain information to generate and then output a force data signal. The force data signal is sent to an I/O device corresponding to the surgical instrument identified by the unique identifier and presented to surgeon 190.

In one aspect, an indication of the force data signal, e.g., a moving bar graph, is presented in display 111 for the appropriate surgical instrument. In another aspect, the force data signal is used to activate, for example, a pneumatically or electromagnetically actuated pad on the master finger levers, which are used to control the surgical instrument with the unique identifier, to provide haptic force feedback to surgeon 190 for that surgical instrument. In yet another aspect, actuators on the finger levers respond by applying a force on the master finger levers, which in turn apply force on the surgeon's fingers. Alternatively, or in some combination, an audible signal can be used to provide force feedback to surgeon 190.

In some aspects, surface acoustic wave strain sensor with identification information 390B may be sensitive to temperature. In addition to the effects due to strain changes associated with applying loads to the law, temperature sensitivity can also affect the reflected waves.

Thus, in one aspect, it may be advantageous to use a calibration process in which forces are applied to the instrument jaws while the jams are held at about human body temperature. Such a calibration process may be done either by directly calculating the correction factors and offsets or by a learning system such as a neural network embedded in the calibration fixture or in the instrument itself. In any calibration method, the calibration data may be programmed into an integrated circuit embedded in the surgical instrument so that the surgical system using the individual instrument can correctly identify and apply its correction factors and offsets while the surgical instrument is in use.

In addition or alternatively, the temperature effects can be mitigated by selection of the piezoelectric substrate and/or use of a temperature-compensated cut of the substrate material. Also, the surgical instrument including wireless force sensor 375B can be maintained in a stable thermal environment. For example, at least the distal end of the surgical instrument can be maintained in a bath or in a shroud to keep the instrument at about human body temperature. In one aspect, the shroud, e.g., radio-frequency shield pocket 255 (FIG. 2A), also shields the wireless force sensor from any interrogation signals.

In a surgical procedure prior to use, the surgical instrument is placed in such a human body temperature environment until the temperature stabilizes and then is used in the surgery. If during surgery, the surgical instrument is temporarily removed from the patient, the distal end of the surgical instrument is placed back in the temperature stabilization device, which was referred to above as a shroud. In this way, the temperature of the surface acoustic wave strain sensor remains substantially constant and so temperature effects are minimized. In another aspect, a chirped surface acoustic wave device (FIGS. 2E to 2G and 3G) rejects a uniform temperature disturbance along the sensor because the temperature change shifts the entire frequency response of the chirped surface acoustic wave device while strain gradients along the law due to forces applied to the jaw widen or narrow the frequency response.

In the above aspects, interrogator antenna 400 was outside the patient, and so the wireless signals have to penetrate the patient undergoing surgery. However, in another aspect, an interrogator antenna 400B (FIG. 4B) is mounted on a distal end of another surgical instrument, e.g., endoscope 431, which is connected to wireless interrogator 160A by a wired connection. Advantageously, such an antenna may be larger and offer better coupling to the small folded surface acoustic wave strain sensor antenna.

Surgical instruments 430 and 431 are both used in the surgical operation and so are both within the patient during the surgery. During the surgery, interrogator antenna 400B transmits the wireless interrogation signal to wireless force sensor 475 mounted on a distal portion of surgical instrument 430.

Wireless force sensor 475 receives the wireless interrogation signal and in response thereto, transmits strain data and identification information that is received by interrogator antenna 400B. The closer proximity of interrogator antenna 400B and wireless force sensor 475 coupled with removing the need for the wireless signal to penetrate into and out of the patient allows use of relatively weaker wireless signal strengths. This may help to reduce any interference problems with other instruments or equipment used in the operating room or in adjacent operating rooms.

Specifically, the low interrogation signal strength coupled with the fact that the interrogation signal is attenuated as the signal penetrates out of the patient reduces the interrogation signal strength that reaches the operating room or adjacent operating rooms. The reduced interrogation signal strength in the operating rooms also reduces the likelihood that wireless force sensors on different surgical instruments in the operating room or in adjacent operating rooms may receive and respond to the interrogation signal.

It is noted that various surgical instruments may be improved in accordance with the present invention, including but not limited to tools with and without surgical end effectors, such as laws, scissors, graspers, needle holders, micro-dissectors, staple appliers, tickers, suction irrigation tools, clip appliers, irrigators, catheters, and suction orifices. Alternatively, the surgical instrument may comprise an electrosurgical probe for ablating, or coagulating tissue. Such surgical instruments are available from. Intuitive Surgical, Inc. of Sunnyvale, Calif.

Various other locations of force sensors can be utilized on a surgical instrument. Referring to FIG. 5, a perspective view is shown of a surgical instrument 530 including a force sensor apparatus 500 operably coupled to a distal end of a rigid shaft 510 and proximal to a wrist joint 521 in accordance with an embodiment of the present invention. An end portion 520, such as a surgical end effector, is coupled to force sensor apparatus 500 via wrist joint 521. A housing 550 is operably coupled to a proximal end of rigid shaft 510 and includes an interface 552 which mechanically and electrically couples instrument 530 to a manipulator assembly.

Figure 6A:
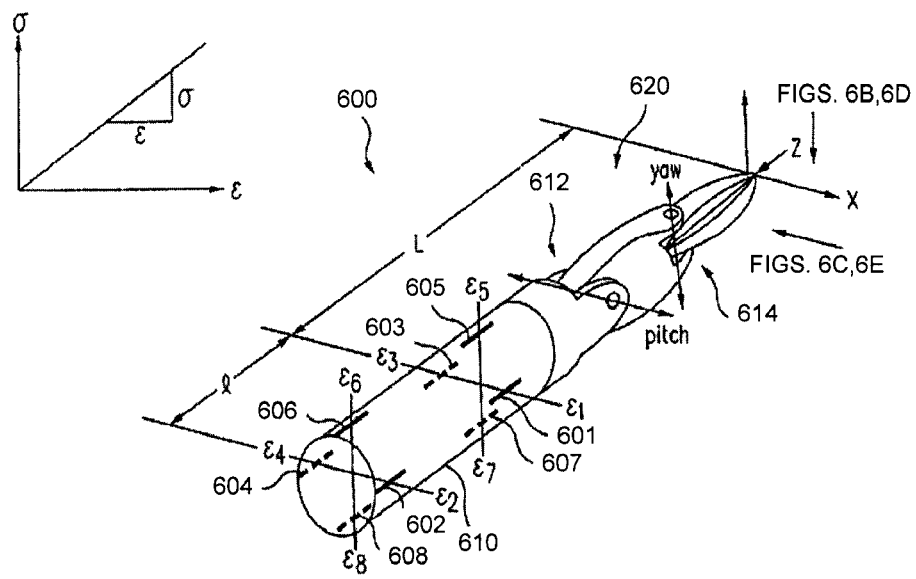
FIG. 6A is a perspective view of a surgical instrument distal end showing a wrist, grip jaws, and force sensors for use with a telerobotic surgical system.

In an alternative embodiment, an instrument portion of a surgical instrument includes strain sensors that are used to measure force. FIG. 6A shows a perspective view of a portion 600 of a surgical instrument that includes a shaft 610, wrist joints 612 and 614, and an end portion 620 that may be used to manipulate a surgical tool and/or contact the patient. The surgical instrument also includes a housing that operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In one configuration, end portion 620 has a range of motion that includes pitch and yaw motion about the x- and y-axes and rotation about the z-axis (as shown in FIG. 6A). These motions, as well as actuation of an end effector, are done via cables running through shaft. 610 and housing 650 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as laws, scissors, graspers, needle holders, micro-dissectors, staple appliers, tackers, suction irrigation tools, clip appliers, irrigators, catheters, and suction orifices. Alternatively, the surgical instrument may comprise an electrosurgical probe for ablating, or coagulating tissue. Such surgical instruments are commercially available from Intuitive Surgical, Inc. of Sunnyvale, Calif.

In accordance the embodiment of FIGS. 6A to 6E, instrument portion 600 includes sensors (e.g., strain gauges) mounted onto the exterior surface of shaft 610, oriented parallel to the longitudinal (lengthwise) axis of the shaft, termed the z-axis. The two axes perpendicular to the shaft are called the x- and y-axes. The signals from the sensors are combined arithmetically in various sums and differences to obtain measures of three perpendicular forces (e.g., $F_x$, $F_y$, and $F_z$) exerted upon the instrument tip and the torques (Tx, Ty) about the two axes perpendicular to the shaft axis (i.e., the x- and y-axes). The measurement of the forces is made independent of the orientation and effective lever arm length of a wrist mechanism at the distal end of the instrument. Forces exerted against end portion 620 are detected by the force sensing elements, which may be operably coupled to servo control via an interrogator or a processor for transmitting these forces to master(s).

In the embodiment of FIG. 6A, eight strain gauges 601, 602, 603, 604, 605, 606, 607, and 608 are mounted to the outer surface of shaft 610 or in shallow recesses near the outer surface and provide strain data $\varepsilon_1$, $\varepsilon_2$, $\varepsilon_3$, $\varepsilon_4$, $\varepsilon_5$, $\varepsilon_6$, $\varepsilon_7$, and $\varepsilon_8$, respectively. The primary strain sensing direction of the gauges are oriented parallel to the z-axis. The eight strain gauges are mounted in two groups of four, wherein the four gauges in one group are spaced equally, 90 degrees apart around the circumference of the shaft at one axial position (i.e., forming two "rings" of four strain gauges each).

One group of four (e.g., gauges 601, 603, 605, and 607) is mounted proximal to a wrist mechanism as close to a distal end of shaft 610 as possible. The second group of four (e.g., gauges 602, 604, 606, and 608) is mounted at a chosen distance "l" from the first group of four (toward a proximal end of shaft 610) and aligned with them so that pairs of gauges in the two groups are aligned with each other (i.e., gauges 601 and 602, 603 and 604, 605 and 606, and 607 and 608 are aligned).

The z-axis force ($F_z$) including both surgical forces and wrist cable forces is found from the sum of the eight gauge outputs multiplied by a factor of EA/8, where E is the shaft material modulus of elasticity in the z-axis direction, and A is the cross-sectional area of the shaft. The lateral forces along the x- and y-axes ($F_x$, and $F_y$) at or near the tip are found from the difference of the gauge outputs of a pair of gauges on opposite sides of the shaft and the difference between the pair differences along the shaft multiplied by a factor of EI/2rl, where E is the shaft material modulus of elasticity in the z-axis direction, I is the shaft section moment of inertia, r is the radius from the shaft axis to the acting plane of the gauges, and l is the distance between the two groups of four gauges The calculations of the forces are derived from the following equations.

With respect to FIG. 6A, $$E = \sigma/\varepsilon$$

$$A = \pi(r_o^2 - r_i^2)$$

$$I = (\pi/4)(r_o^4 - r_i^4)$$

$$\sigma = (F/A) + (Mr/I)$$

$$\varepsilon = [\varepsilon_1 \; \varepsilon_2 \; \varepsilon_3 \; \varepsilon_4 \; \varepsilon_5 \; \varepsilon_6 \; \varepsilon_7 \; \varepsilon_8]$$

$$\underbrace{\begin{bmatrix} 1 \\ -1 \\ -1 \\ 1 \\ 0 \\ 0 \\ 0 \\ 0 \end{bmatrix}}_{F_x} EI/2lr \quad \underbrace{\begin{bmatrix} 0 \\ 0 \\ 0 \\ 0 \\ 1 \\ -1 \\ -1 \\ 1 \end{bmatrix}}_{F_y} EI/2lr \quad \underbrace{\begin{bmatrix} 1 \\ 1 \\ 1 \\ 1 \\ 1 \\ 1 \\ 1 \\ 1 \end{bmatrix}}_{F_z} - EA/8$$

Figure 6B:
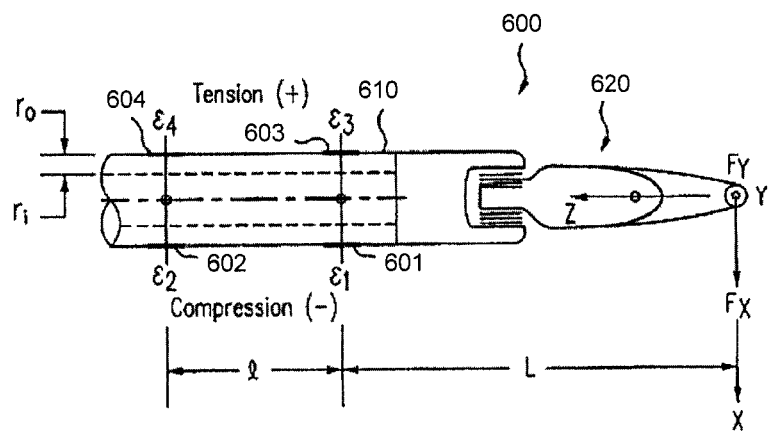
FIG. 6B is a first top view of the surgical instrument of FIG. 6A showing applied forces.
Figure 6C:
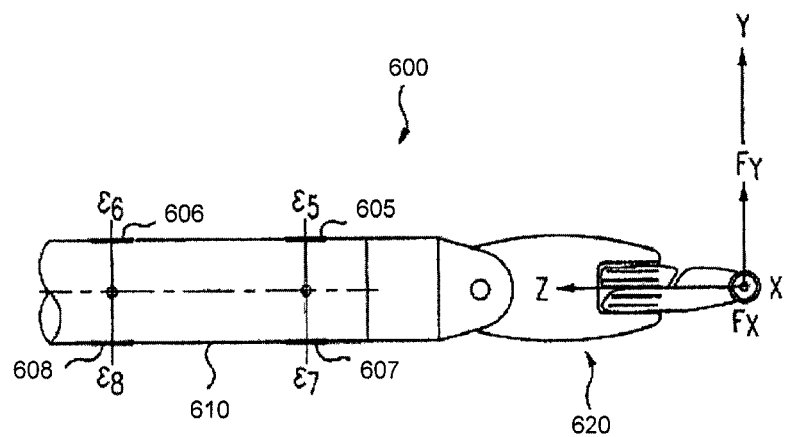
FIG. 6C is a first side view of the surgical instrument of FIG. 6A showing applied forces.

With respect to FIGS. 6B and 6C, $$A = \pi(r_o^2 - r_i^2)$$

$$I = (\pi/4)(r_o^4 - r_i^4)$$

$$\sigma = Mr/I$$

$$\sigma_1 = FLr/I$$

$$\sigma_2 = F(L+l)r/I$$

$$E = \sigma/\varepsilon \Rightarrow \varepsilon = \sigma/E$$

$$\varepsilon_1 = F_x Lr/EI$$

$$\varepsilon_2 = F_x(L+l)r/EI$$

$$\varepsilon_2 - \varepsilon_1 = -F_x lr/EI$$

$$\varepsilon_4 - \varepsilon_3 = F_x lr/EI$$

$$(\varepsilon_4 - \varepsilon_3) - (\varepsilon_2 - \varepsilon_1) = 2F_x lr/EI$$

Thus, $$(\varepsilon_1 - \varepsilon_2 - \varepsilon_3 + \varepsilon_4)EI/2lr = F_x$$

$$(\varepsilon_5 - \varepsilon_6 - \varepsilon_7 + \varepsilon_8)EI/2lr = F_y$$

$$(\varepsilon_1 + \varepsilon_2 + \varepsilon_3 + \varepsilon_4 + \varepsilon_5 + \varepsilon_6 + \varepsilon_7 + \varepsilon_8)EA/8 = F_z$$

$F_x$ and $F_y$ are thus invariant with respect to L and invariant with respect to temperature at steady state.

Advantageously, the measured transverse forces ($F_x$, $F_y$) at the instrument tip are independent of variations in the effective lever arm length due to wrist orientation changes or gripping position changes in the end portion during surgery. The measured transverse forces are also independent of changes in the z-axis forces especially those due to the varying wrist cable tensions. Further, the measured transverse forces are independent of both surgical and wrist friction induced torques applied distal to the combined groups of strain gauges. Finally, the measured forces along the x- and y-axes are independent of temperature changes when at thermal equilibrium over all gauges. This may be seen by adding an equal temperature disturbance strain to all four gauges in the equations for $F_x$ and $F_y$ and noting that the disturbances cancel. Thermal transients during which gauge temperatures are unequal are not compensated by this design although other measures may be taken to do so.

The measurements of the torques about the x- and y-axes ($T_x$ and $T_y$) at the instrument tip are derived from the differences of the gauges paired across the shaft diameter and the sum of the pair differences along the shaft axis multiplied by a factor EI/4r, wherein once again F is the shaft material modulus of elasticity in the axial direction, I is the shaft section moment of inertia, and r is the radius from the shaft axis to the acting plane of the gauges. Thus the forces ($F_x$, $F_y$, $F_z$) and torques ($T_x$, $T_y$) exerted at the instrument tip are measured without errors due to wrist orientation or the location of a gripped tool such as a suture needle within laws or tissue held in a grasper, for example. Torque measurements about the x- and y-axes are also independent of temperature at steady state. The calculations of the torques are derived from the following equations.

Figure 6D:
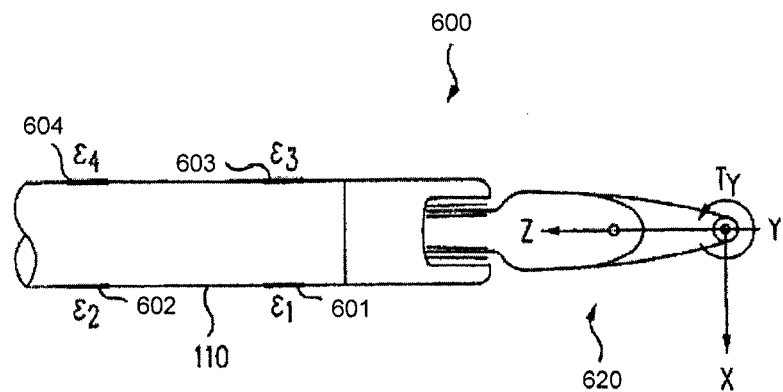
FIG. 6D is a second top view of the surgical instrument of FIG. 6A showing applied torque.
Figure 6E:
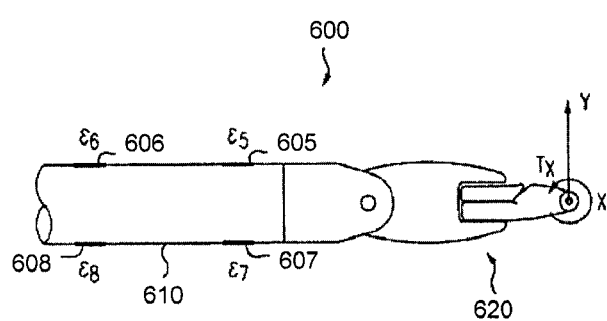
FIG. 6E is a second side view of the surgical instrument of FIG. 6A showing applied torque.

With respect to FIGS. 6D and 6E in conjunction with FIG. 6A, $$\underbrace{\begin{bmatrix} 0 \\ 0 \\ 0 \\ 0 \\ -1 \\ -1 \\ 1 \\ 1 \end{bmatrix}}_{T_x} EI/4r \quad \underbrace{\begin{bmatrix} 1 \\ 1 \\ -1 \\ -1 \\ 0 \\ 0 \\ 0 \\ 0 \end{bmatrix}}_{T_y} EI/4r$$

$$\sigma = Mr/I$$
$$\sigma_1 = \sigma_2 = Tr/I$$
$$E = \sigma/\varepsilon = > \varepsilon = \sigma/E$$
$$\varepsilon_1 = \varepsilon_2 = Tr/EI$$

Thus, $$(\varepsilon_1+\varepsilon_2-\varepsilon_3-\varepsilon_4)EI/4r=T_y$$

$$(-\varepsilon_5-\varepsilon_6+\varepsilon_7+\varepsilon_8)EI/4r=T_x$$

While the embodiment described with respect to FIGS. 6A to 6E may be applied to surgical instruments of many constructions, it is of particular value for use with anisotropic linear fiber reinforced polymer tubing, in one example, because all gauges are oriented parallel to the z-axis with constant and easily characterized elastic properties. Similar advantages may be gained with properly characterized woven reinforced tubing, and the method is also applicable to uniform elastic property tubing.

In one example, various strain gauges may be used, including but not limited to conventional foil type resistance gauges, semiconductor gauges, optic fiber type gauges using Bragg grating or Fabry-Perot, technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

Both fiber technologies require an interrogator unit that decodes the optically encoded strain information into electrical signals compatible with the computer control hardware or display means of the minimally invasive surgical system. A processor may then be used to calculate forces according to the signals from the strain gauges/sensors.

In one aspect, the fiber Bragg gratings and the optic fibers are replaced with a wireless package including a small folded antenna and a surface acoustic wave strain sensor with identification information, as described above. In this aspect, the identification information includes information that not only uniquely identifies the particular surgical instrument, but also identifies the location of the surface acoustic wave strain sensor with identification information. This permits associating the strain information with a particular location on force sensor 600. Alternatively, multiple surface acoustic wave based force sensors could be distinguished by frequency of the signal from each of the force sensors.

The above description and the accompanying drawings that illustrate aspects and embodiments of the present inventions should not be taken as limiting the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms such as "beneath", "below", "lower", "above", "upper", "proximal", "distal", and the like may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

All examples and illustrative references are non-limiting and should not be used to limit the claims to specific implementations and embodiments described herein and their equivalents. The headings are solely for formatting and should not be used to limit the subject matter in any way, because text under one heading May cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the invention. It should also be understood that numerous modifications and variations are possible in accordance with the principles of the present invention. For example, the number of strain sensors and their configuration may vary but must allow for applicable force determinations and noise rejection. Furthermore, the embodiments of force sensor apparatus described above may be integrated with a surgical instrument upon manufacture as a non-separable part. Accordingly, the scope of the invention is defined only by the following claims.

We claim:

1. A surgical instrument comprising:
a shaft having an exterior surface:
a wrist joint coupled to the shaft; and
a surgical end effector mounted distal to said wrist joint, the surgical instrument comprising a jaw portion, the jaw portion having an external non-contact surface bounding a contact surface, wherein a force sensor is mounted on the non-contact external surface, the force sensor comprising:
a wireless package comprising a surface acoustic wave strain sensor and a folded antenna, the folded antenna being electrically coupled to the surface acoustic wave strain sensor.

2. The surgical instrument of claim 1, wherein the jaw portion comprises an electrically non-conductive material.

3. The surgical instrument of claim 1, wherein said surface acoustic wave strain sensor comprises a chirped surface acoustic wave strain sensor.

4. The surgical instrument of claim 1, wherein the surface acoustic wave strain sensor includes identification information of the surgical instrument.

5. The surgical instrument of claim 4, wherein said identification information includes an identification of a type of said surgical instrument.

6. The surgical instrument of claim 5, wherein said identification information further includes identification information unique to said surgical instrument.

7. The surgical instrument of claim 4, wherein said identification information includes identification information unique to said surgical instrument.

8. The surgical instrument of claim 1, further comprising:
a radio-frequency shield pocket mounted on said jaw portion of said surgical instrument.

9. The surgical instrument of claim 1, further comprising:
an interrogator antenna configured to transmit wireless interrogation signals to said wireless package, and to receive, from said wireless package, a wireless signal; and
a wireless interrogator, coupled to said interrogator antenna, to receive signals from said interrogator antenna.

10. The surgical instrument of claim 9, wherein said interrogator antenna is located external to a patient undergoing surgery.

11. The surgical instrument of claim 9, further comprising:
a computer connected to said wireless interrogator to receive a signal including (1) identification information of said surgical instrument and (2) strain data from said jaw portion, and to convert said strain data into a force signal wherein said force signal is used to provide feedback to a surgeon operating said surgical instrument.

12. The surgical instrument of claim 1, wherein a plurality of force sensors are mounted onto the exterior surface of the shaft.

13. A method comprising:
receiving a wireless interrogation signal in a wireless package, the wireless package comprising a surface acoustic wave strain sensor and a folded antenna, the folded antenna being electrically coupled to the surface acoustic wave strain sensor, wireless package being mounted an external non-contact surface of a jaw portion of a surgical instrument, the external non-contact surface bounding a contact surface of the jaw portion; and
transmitting from said wireless package, in response to said wireless interrogation signal, a wireless signal including identification information of said surgical instrument.

14. The method of claim 13, further comprising receiving, by an antenna of an interrogator, the wireless signal including the identification information;
outputting, the interrogator in response to the received wireless signal including the identification information, a digital signal to a control system; and
outputting, by the control system in response to the digital signal, force data to an input/output device identified using the identification information.

\* \* \* \* \*

UNITED STATES PATENT AND TRADEMARK OFFICE
CERTIFICATE OF CORRECTION

PATENT NO. : 10,363,107 B2
APPLICATION NO. : 15/938440
DATED : July 30, 2019
INVENTOR(S) : Blumenkranz et al.

It is certified that error appears in the above-identified patent and that said Letters Patent is hereby corrected as shown below:

On the Title Page

On page 2, in Column 2, item (56), under "Other Publications", Line 4, delete "minimaliy" and insert --minimally-- therefor In the Claims In Column 22, Line 19, in Claim 14, delete "comprising" and insert --comprising:¶-- therefor Signed and Sealed this
Twenty-fourth Day of March, 2020

Andrei Iancu
*Director of the United States Patent and Trademark Office*